(12) United States Patent
Hagihara et al.

(10) Patent No.: US 8,029,438 B2
(45) Date of Patent: Oct. 4, 2011

(54) ENDOSCOPE AND HYDROPHILIC CAP

(75) Inventors: Masahiro Hagihara, Hachioji (JP);
Takao Yamaguchi, Hachioji (JP);
Kiyoshi Tsuji, Kunitachi (JP); Atsushi Goto, Oume (JP); Hiroaki Kinoshita, Akishima (JP); Hirofumi Yamamoto, Hino (JP)

(73) Assignee: Olympus Medical Systems Corp., Tokyo (JP)

(*) Notice: Subject to any disclaimer, the term of this patent is extended or adjusted under 35 U.S.C. 154(b) by 635 days.

(21) Appl. No.: 12/129,326

(22) Filed: May 29, 2008

(65) Prior Publication Data

US 2008/0228035 A1    Sep. 18, 2008

Related U.S. Application Data

(63) Continuation of application No. PCT/JP2006/321272, filed on Oct. 25, 2006.

(30) Foreign Application Priority Data

Dec. 1, 2005    (JP) .................................. 2005-348392

(51) Int. Cl.
*A61B 1/07* (2006.01)
(52) U.S. Cl. ........ 600/169; 600/127; 600/129; 600/133; 600/176; 600/182
(58) Field of Classification Search .................. 600/127, 600/129, 133, 169
See application file for complete search history.

(56) References Cited

U.S. PATENT DOCUMENTS

| | | | | |
|---|---|---|---|---|
| 4,279,246 A | * | 7/1981 | Chikama | 600/169 |
| 4,876,126 A |   | 10/1989 | Takemura et al. | |
| 5,347,990 A |   | 9/1994 | Ebling et al. | |
| 5,518,502 A | * | 5/1996 | Kaplan et al. | 600/157 |
| 5,575,756 A | * | 11/1996 | Karasawa et al. | 600/157 |
| 5,605,532 A | * | 2/1997 | Schermerhorn | 600/169 |
| 5,647,840 A | * | 7/1997 | D'Amelio et al. | 600/169 |
| 5,702,754 A | * | 12/1997 | Zhong | 427/2.12 |
| 5,842,971 A | * | 12/1998 | Yoon | 600/101 |
| 6,048,620 A | * | 4/2000 | Zhong | 428/424.4 |

(Continued)

FOREIGN PATENT DOCUMENTS

DE    20 2004 005 783    6/2004

(Continued)

OTHER PUBLICATIONS

Communication Pursuant to Article 94(3) EPC mailed Dec. 7, 2010 in related European Patent Application No. 06822249.6.

(Continued)

*Primary Examiner* — Matthew J Kasztejna
(74) *Attorney, Agent, or Firm* — Scully, Scott, Murphy & Presser, P.C.

(57) ABSTRACT

An endoscope includes: an insertion portion including a distal end portion, to be inserted into a subject; an observation optical system disposed in the insertion portion; an optical member configuring a part of an outer surface of the distal end portion, through which a photographing light to be incident into the observation optical system transmits; a first hydrophilic portion that is film-formed at least on a surface of the optical member; a second hydrophilic portion that is film-formed on a first surface of the distal end portion in which the optical member is disposed; and a third hydrophilic portion that is film-formed on a second surface separate from the first surface of the distal end portion.

9 Claims, 18 Drawing Sheets

U.S. PATENT DOCUMENTS

| | | | |
|---|---|---|---|
| 6,503,196 B1 * | 1/2003 | Kehr et al. | 600/176 |
| 2003/0023190 A1 | 1/2003 | Cox | |
| 2006/0069312 A1 | 3/2006 | O'Connor | |

FOREIGN PATENT DOCUMENTS

| | | |
|---|---|---|
| JP | HEI 2-62412 | 5/1990 |
| JP | 7-275185 | 10/1995 |
| JP | 08-056895 | 3/1996 |
| JP | 08-252210 | 10/1996 |
| JP | 10-043128 | 2/1998 |
| JP | 11-047081 | 2/1999 |
| JP | 2000-079086 | 3/2000 |
| JP | 2000-300570 | 10/2000 |
| JP | 2001-128932 | 5/2001 |
| JP | 2001-128933 | 5/2001 |
| JP | 2001-149313 | 6/2001 |
| JP | 2002-330924 A | 11/2002 |
| JP | 2004-267583 | 9/2004 |
| JP | 2005-144001 A | 6/2005 |
| JP | 2005-312809 | 11/2005 |
| WO | WO 97/31293 A1 | 8/1997 |
| WO | WO 2004/080294 A1 | 9/2004 |

OTHER PUBLICATIONS

European Search Report mailed Jun. 21, 2011 in corresponding European Patent Application No. 11002840.4.

* cited by examiner

WATER REPELLENT  UNPROCESSED  HYDROPHILIC
$\theta > 80°$        $\theta \fallingdotseq 50°$      $\theta < 20°$

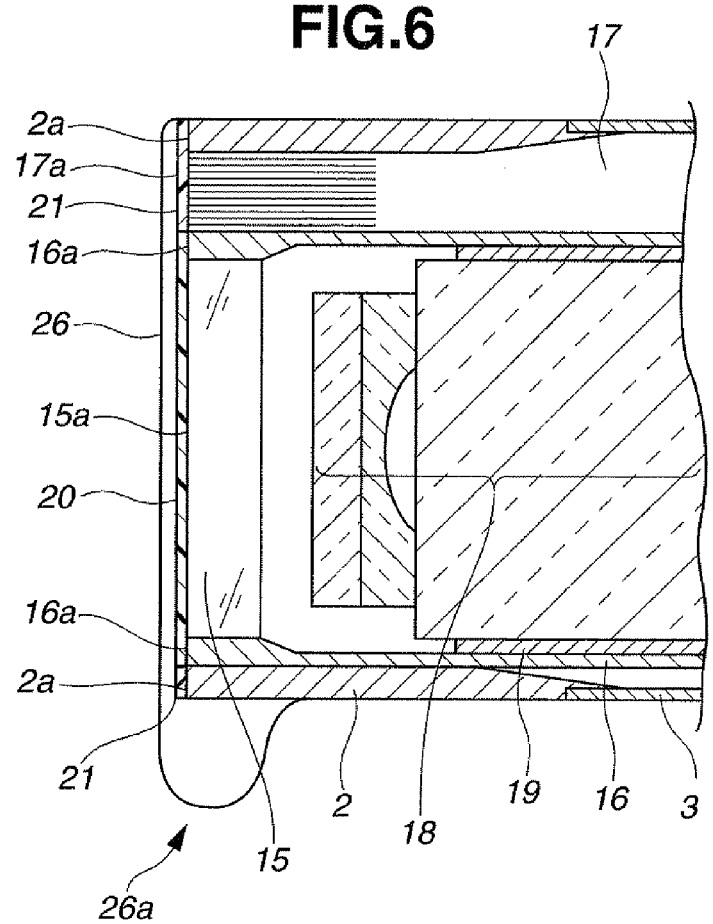
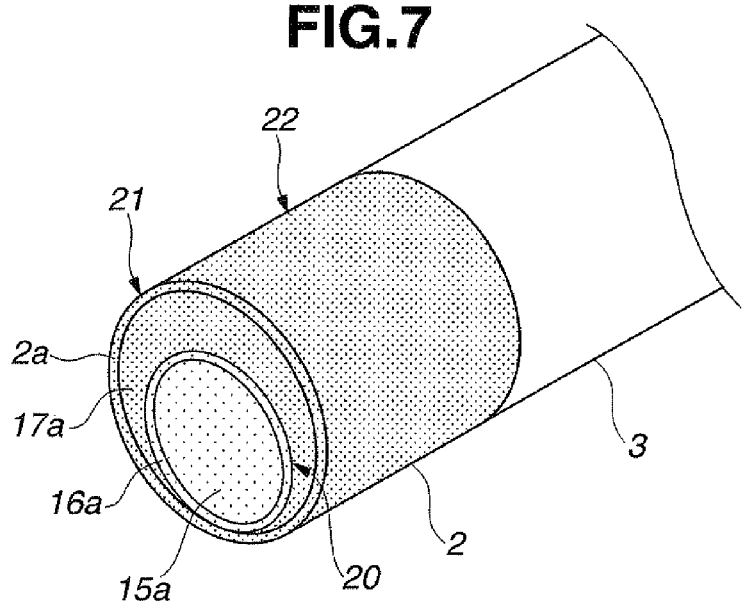

US 8,029,438 B2

ENDOSCOPE AND HYDROPHILIC CAP

CROSS REFERENCE TO RELATED APPLICATION

This application is a continuation application of PCT/JP2006/321272 filed on Oct. 25, 2006 and claims benefit of Japanese Application No. 2005-348392 filed on Dec. 1, 2005, the entire contents of which are incorporated herein by this reference.

BACKGROUND OF THE INVENTION

1. Field of the Invention

The present invention relates to an endoscope having an insertion portion including an image pickup portion to be inserted into a body cavity or an abdominal cavity during diagnosis, inspection or therapy, and to a hydrophilic cap to be attached to this endoscope.

2. Description of the Related Art

In recent years, endoscopes have been widely used that can perform diagnosis, inspection or therapy of organs, biological tissues, etc., in a body cavity or abdominal cavity. The endoscopes include, for example: a flexible endoscope including a flexible insertion portion to be inserted from an anus or oral cavity into a body cavity such as a large intestine, stomach, etc.; and a rigid endoscope including a rigid insertion portion to be inserted from an incised portion into a body for operation in the abdominal cavity under the endoscope observation.

These endoscopes include a lens unit to obtain an image of an organ, etc., and an image pickup device or an image pickup portion such as a glass fiber-made image guide fiber and a relay lens. On a distal end surface of the insertion portion of the endoscope, a cover member with light transparency is provided in front of the lens unit. A surface of this cover member configures one outer surface of the distal end surface of the insertion portion.

When the insertion portion of the endoscope is inserted into a body cavity or abdominal cavity, the cover member is in some cases fogged because of a temperature difference between the outside air and the inside of the body cavity. Accordingly, to prevent the fogging of the cover member, as described in, e.g., Japanese unexamined patent publication No. 7-275185, a technique is disclosed to remove fogging by covering the insertion portion with a sheath having a cleaning nozzle to spray a fluid on a surface of a cover member subjected to a defogging processing.

Further, as described in, e.g., Japanese Unexamined Patent Publication No. 2004-267583, a technique is disclosed to prevent fogging by forming a thin film containing a photocatalyst on a surface of a cover member for hydrophilization. This endoscope can prevent the fogging because even if the surface of the cover member is adhered with a liquid such as a body fluid in the body cavity or abdominal cavity, water caused by humidity, and a physiological saline solution, the liquid becomes a water film that is evenly wet and spread.

SUMMARY OF THE INVENTION

An endoscope of the present invention includes an insertion portion including a distal end portion, to be inserted into a subject; an observation optical system disposed in the insertion portion; an optical member configuring a part of an outer surface of the distal end portion, through which a photographing light to be incident into the observation optical system transmits; a first hydrophilic portion that is film-formed at least on a surface of the optical member; a second hydrophilic portion that is film-formed on a first surface of the distal end portion in which the optical member is disposed; and a third hydrophilic portion that is film-formed on a second surface separate from the first surface of the distal end portion.

Further, a hydrophilic cap of the present invention includes: a cylindrical body having an essentially circular ring shape, that is detachably attachable to a distal end portion of an endoscope; a transparent plate body disposed on one end of the cylindrical body; and a hydrophilic portion that is film-formed on a surface of at least the plate body.

According to the present invention described above, there can be realized an endoscope and a hydrophilic cap attachable to and detachable from the endoscope that can clearly photograph an image in a highly humid body cavity even if an operation is performed for a long period of time with the endoscope and the hydrophilic left inserted in the body cavity.

BRIEF DESCRIPTION OF THE DRAWINGS

FIG. 6 relates to the first embodiment, and is a sectional view of a distal end part of the rigid endoscope shown in FIG. 5.

FIG. 7 relates to the first embodiment, and is a plan view showing the distal end surface of the rigid endoscope having the first, second and a third hydrophilic portions.

DETAILED DESCRIPTION OF THE PREFERRED EMBODIMENT(S)

Figure 1:
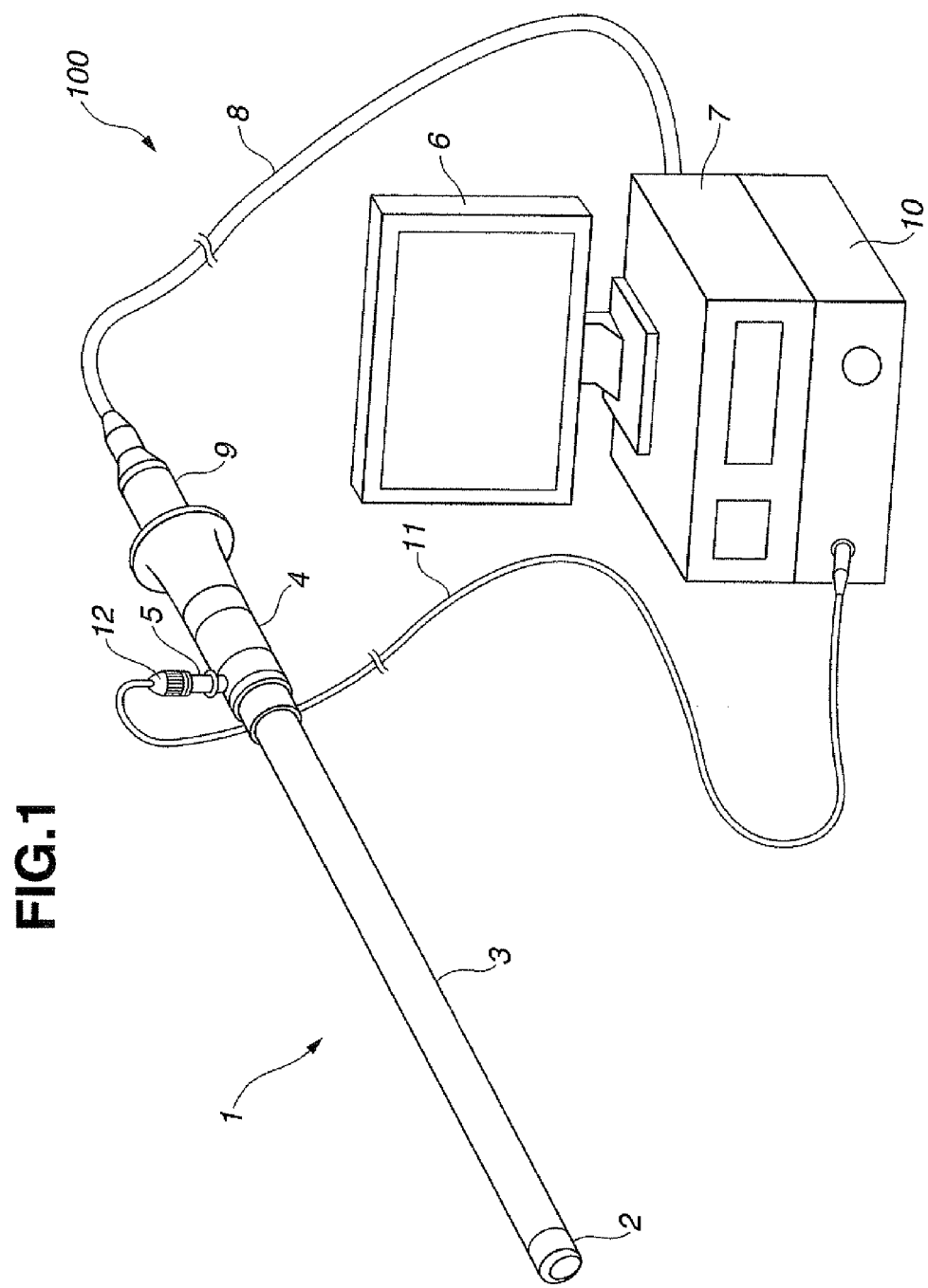
FIG. 1 relates to a first embodiment, and is a general configuration view showing a rigid endoscope system.

Referring to the drawings, embodiments according to an endoscope of the present invention are described below.

First Embodiment

First, a first embodiment of the present invention is described.

Figure 2:
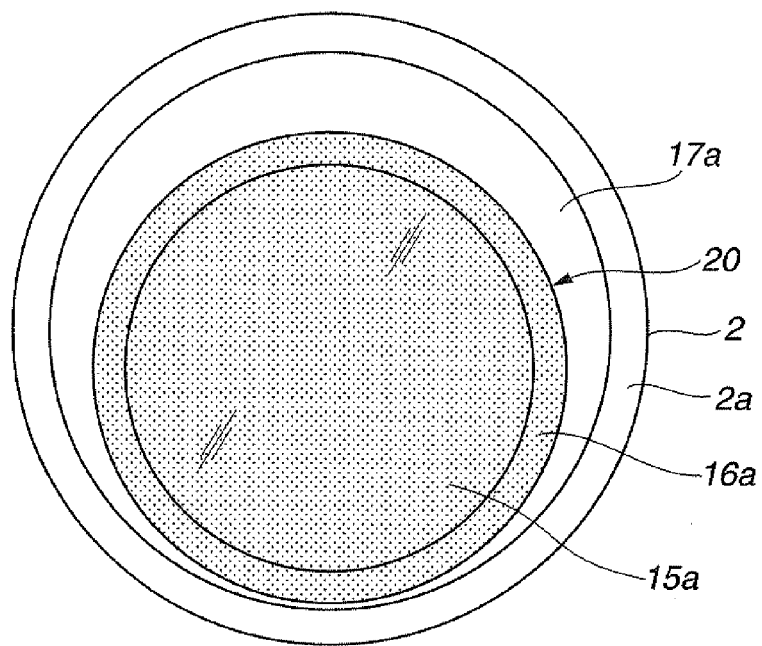
FIG. 2 relates to the first embodiment, and is a plan view showing a distal end surface of a rigid endoscope having a first hydrophilic portion.
Figure 3:
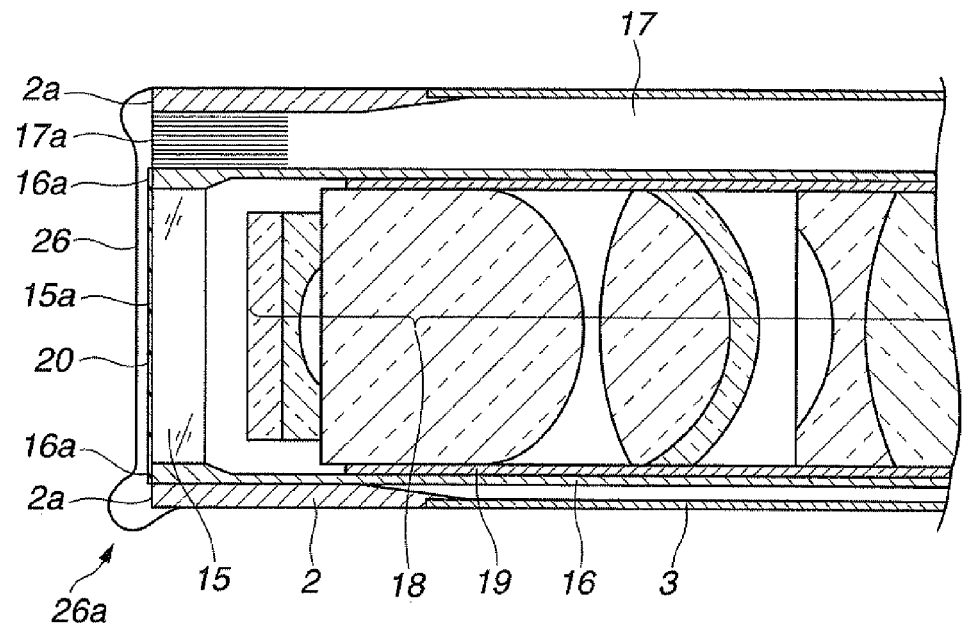
FIG. 3 relates to the first embodiment, and is a sectional view of a distal end part of the rigid endoscope shown in FIG. 2.
Figure 4:
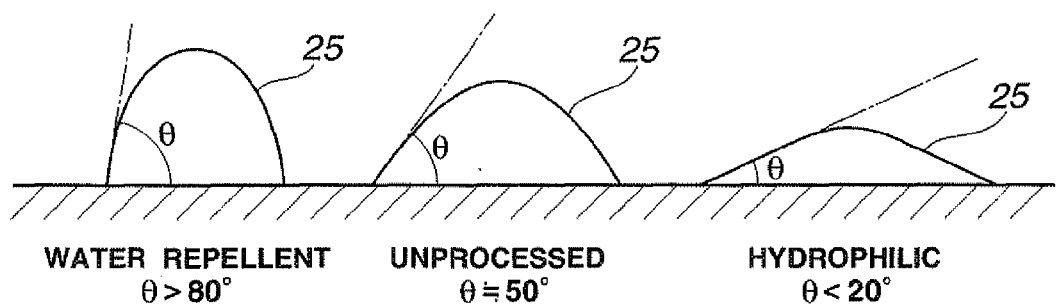
FIG. 4 relates to the first embodiment, and is a view to illustrate definitions of water repellent, unprocessed, and hydrophilic.
Figure 5:
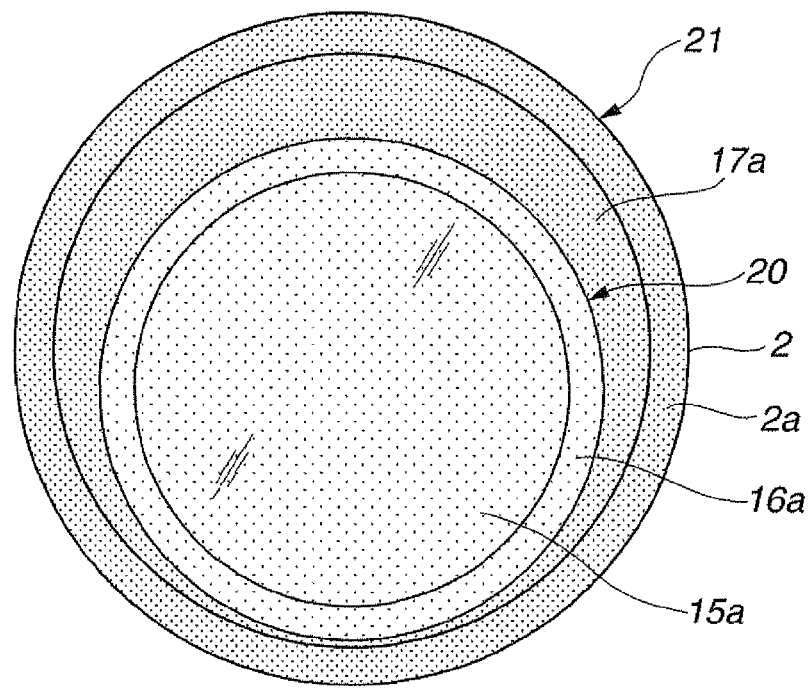
FIG. 5 relates to the first embodiment, and is a plan view showing the distal end surface of the rigid endoscope having the first and a second hydrophilic portions.
Figure 8:
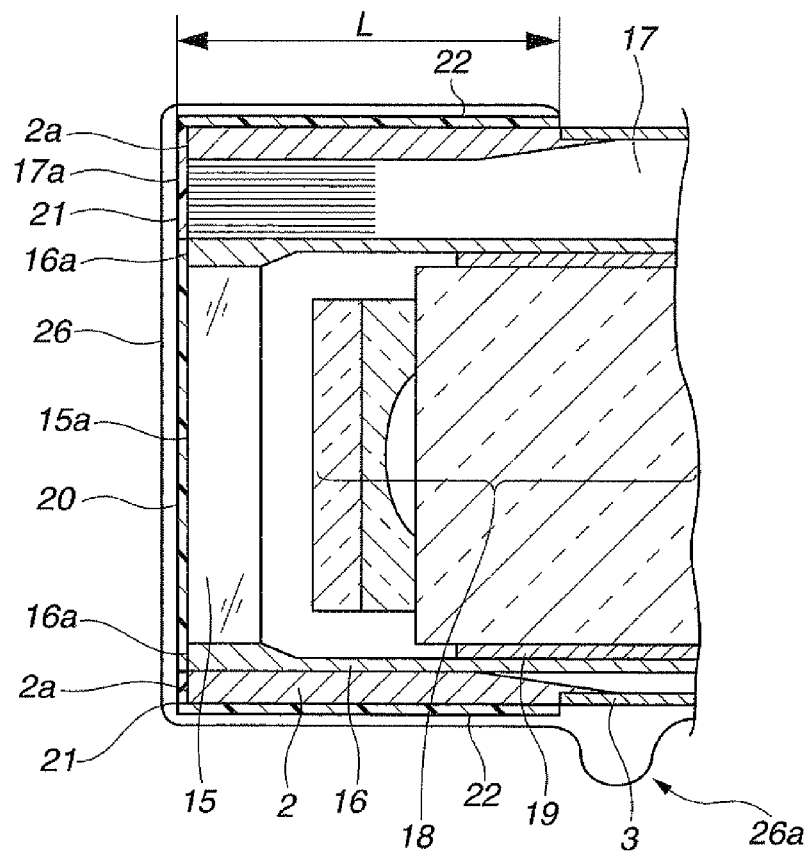
FIG. 8 relates to the first embodiment, and is a sectional view of a distal end part of the rigid endoscope shown in FIG. 7.
Figure 9:
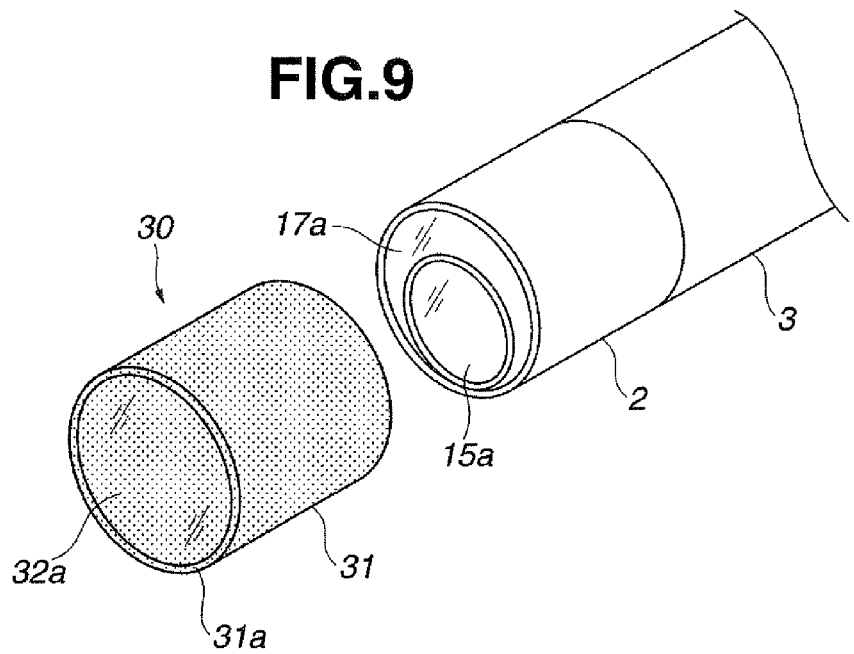
FIG. 9 relates to the first embodiment, and is a perspective view showing a hydrophilic cap that is attachable to and detachable from the distal end portion of the rigid endoscope.
Figure 10:
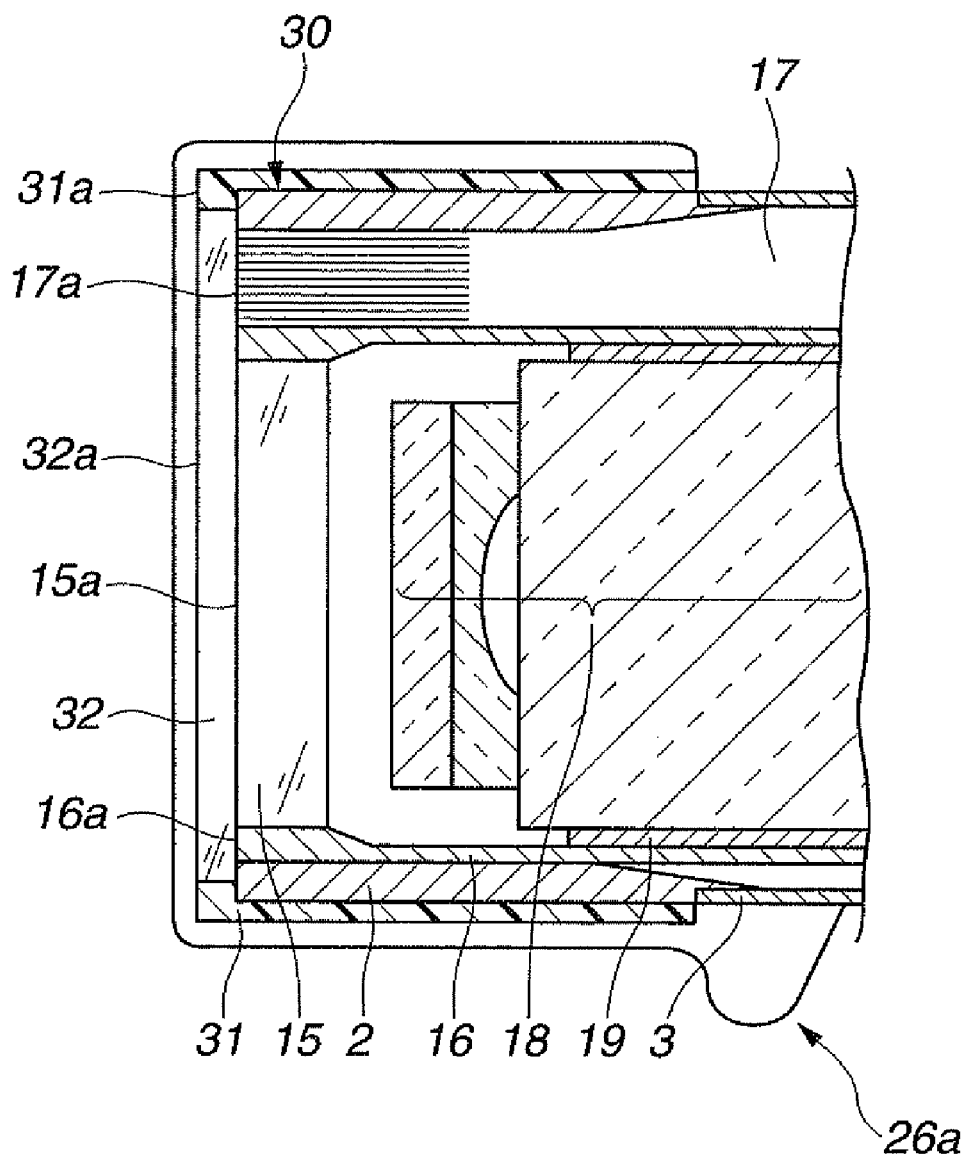
FIG. 10 relates to the first embodiment, and is a sectional view of the distal end part of the rigid endoscope attached with the hydrophilic cap.
Figure 11:
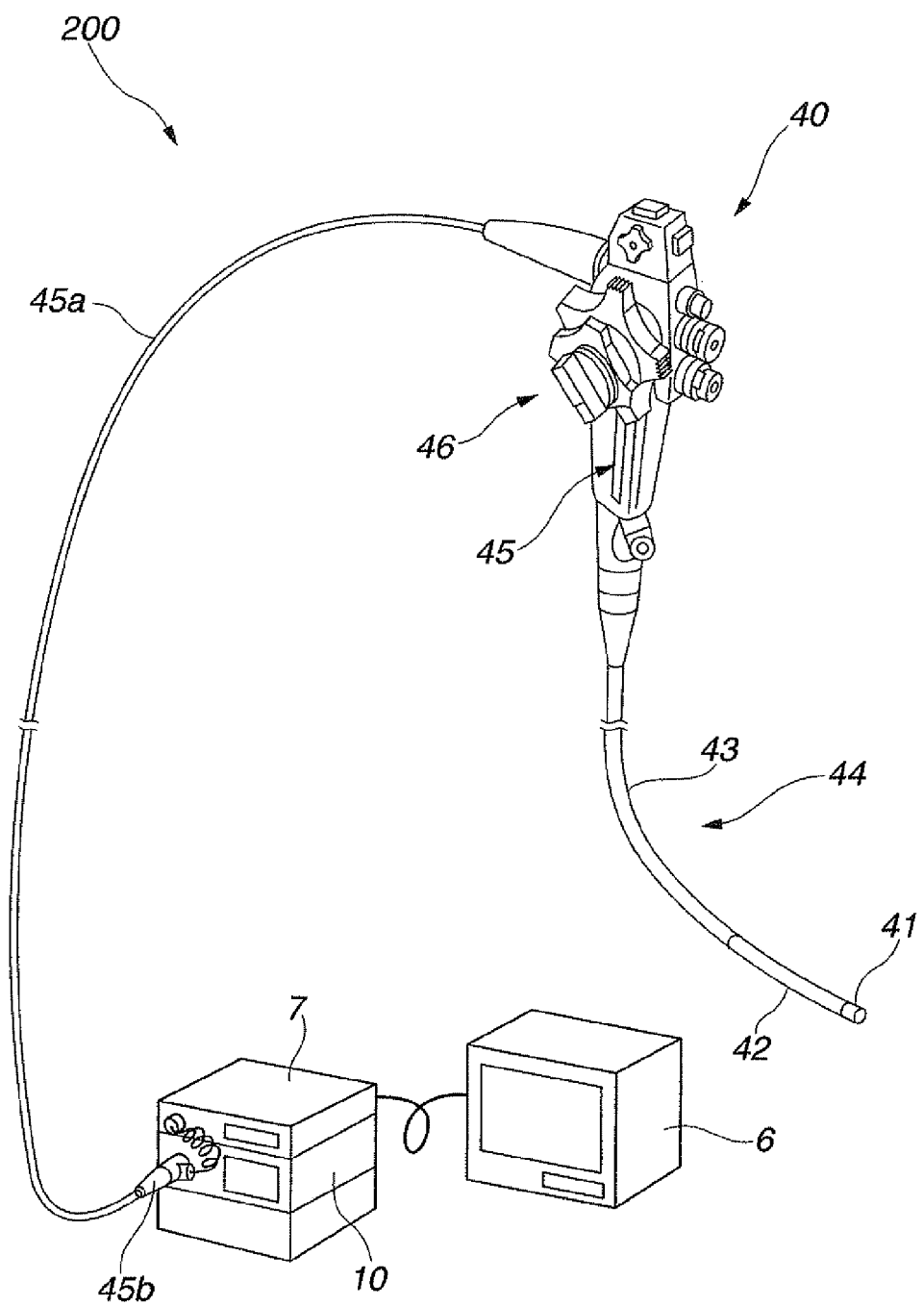
FIG. 11 relates to the first embodiment, and is a general configuration view showing a flexible endoscope system.
Figure 12:
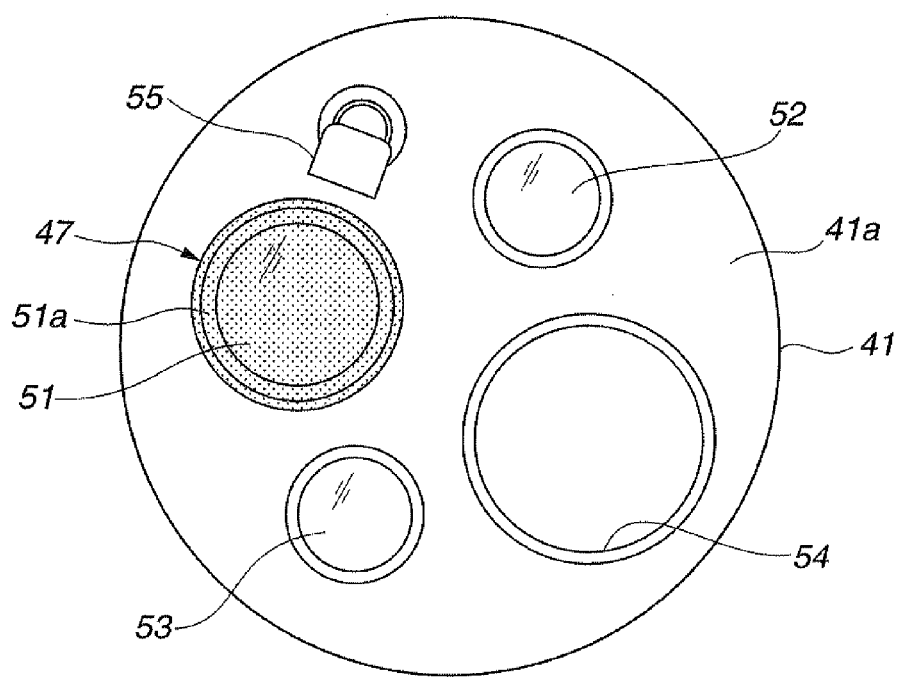
FIG. 12 relates to the first embodiment, and is a plan view showing a distal end surface of a flexible endoscope having a first hydrophilic portion.
Figure 13:
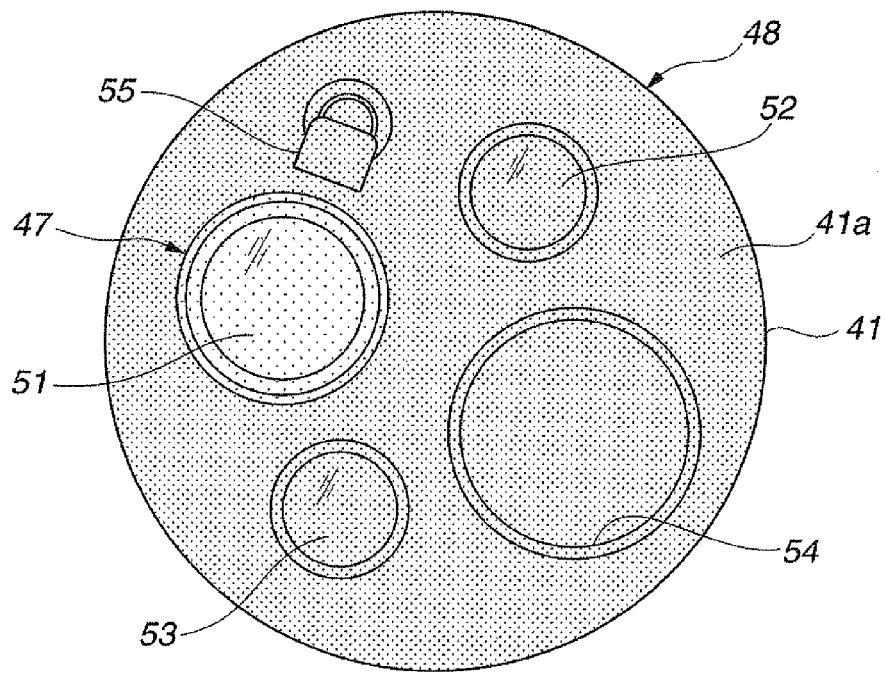
FIG. 13 relates to the first embodiment, and is a plan view showing the distal end surface of the flexible endoscope having the first and a second hydrophilic portion.
Figure 14:
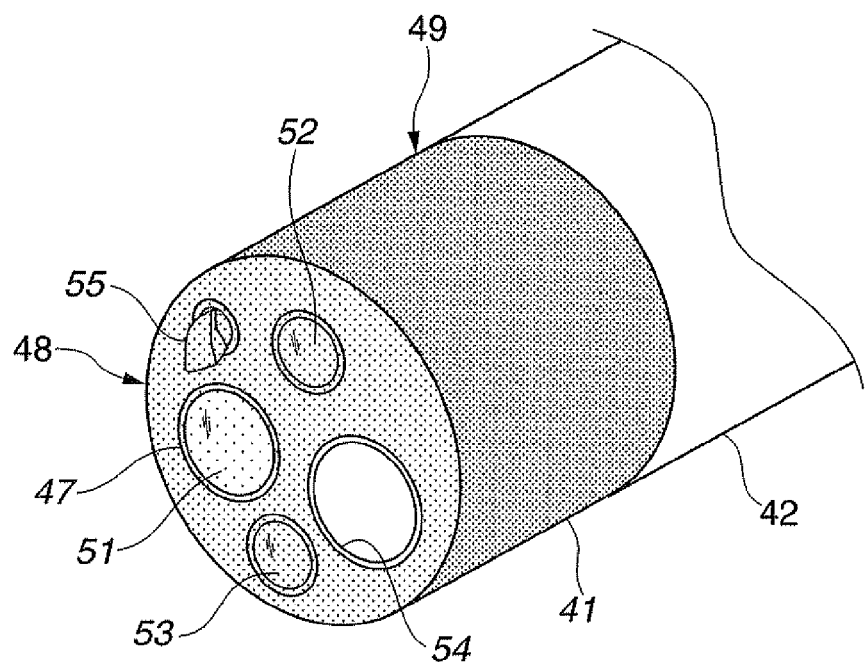
FIG. 14 relates to the first embodiment, and is a plan view showing the distal end surface of the flexible endoscope having the first, second and a third hydrophilic portions.

FIGS. 1 to 14 relate to the first embodiment. FIG. 1 is a general configuration view showing a rigid endoscope system. FIG. 2 is a plan view showing a distal end surface of a rigid endoscope having a first hydrophilic portion. FIG. 3 is a sectional view of a distal end part of the rigid endoscope shown in FIG. 2. FIG. 4 is a view to illustrate definitions of water repellent, unprocessed, and hydrophilic. FIG. 5 is a plan view showing the distal end surface of the rigid endoscope having the first and a second hydrophilic portions. FIG. 6 is a sectional view of a distal end part of the rigid endoscope shown in FIG. 5. FIG. 7 is a plan view showing the distal end surface of the rigid endoscope having the first, second and a third hydrophilic portions. FIG. 8 is a sectional view of a distal end part of the rigid endoscope shown in FIG. 7. FIG. 9 is a perspective view showing a hydrophilic cap that is attachable to and detachable from the distal end portion of the rigid endoscope. FIG. 10 is a sectional view of the distal end part of the rigid endoscope attached with the hydrophilic cap. FIG. 11 is a general configuration view showing a flexible endoscope system. FIG. 12 is a plan view showing a distal end surface of a flexible endoscope having a first hydrophilic portion. FIG. 13 is a plan view showing the distal end surface of the flexible endoscope having the first and a second hydrophilic portions. FIG. 14 is a plan view showing the distal end surface of the flexible endoscope having the first, second and a third hydrophilic portions.

As shown in FIG. 1, a rigid endoscope system 100 includes a rigid endoscope 1, a monitor 6 for displaying an endoscope image, a control unit (hereinafter abbreviated as CCU) 7 which is connected to the monitor 6 and outputs an image-processed endoscope image, and a light source apparatus 10 for outputting illumination light to the rigid endoscope 1.

The rigid endoscope 1 includes a distal end portion 2, a rigid insertion portion 3 which is provided in a linked manner to a proximal end of the distal end portion 2, and a grasping portion 4 which is provided in a linked manner to a proximal end of the insertion portion 3. The grasping portion 4 includes a light guide connector portion 5. The light guide connector portion 5 is connected with a connector portion 12 of a light guide cable 11 connected to the light source apparatus 10. A proximal end of the grasping portion 4 is connected with a camera head 9 incorporating an image pickup device unit comprised of a CCD or CMOS. The camera head 9 is connected to a CCU 7 with an electric cable 8.

As shown in FIGS. 2 and 3, the rigid endoscope 1 includes, on a distal end surface thereof: a glass surface portion 15a of a cover glass 15 which is an optical member having light transparency; a distal end surface 16a of an optical member holding tube 16 for holding the cover glass 15 at a distal end position; and an irradiating surface 17a of a light guide 17 in a region formed between the distal end surface 16a of the optical member holding tube 16 and a distal end surface 2a of the distal end portion 2.

Note that the center axis of the optical member holding tube 16 for holding the cover glass 15 is arranged at a position decentered with respect to the center axis of the distal end portion 2 and the insertion portion 3.

Inside the optical member holding tube 16, there is disposed a lens holding tube 19 for holding an optical (object) lens group 18 including a plurality of lenses configuring an observation optical system, and a group of a plurality of relay lenses not shown and introducing image pickup light condensed by the optical lens group 18 to an image pickup device in the camera head 9.

The image pickup device unit in the camera head 9 converts the condensed image pickup light to an image signal. This image signal is then transmitted to the CCU 7 by the electric cable 8 connected to the camera head 9 shown in FIG. 1.

Note that the rigid endoscope 1 is not limited to one having a relay lens group in the insertion portion 3, but may be one including the image pickup device unit in the insertion portion 3. In such type of the rigid endoscope 1, for example, a communication cable extends from the image pickup unit in the insertion portion 3, to be inserted through the insertion portion 3 and extendedly provided up to the proximal end of the grasping portion 4. The communication cable is electrically connected to an electric cable by a connector connected to the grasping portion 4. This electric cable is connected to the CCU7, so that the condensed image pickup light from the image pickup device unit is transmitted to the CCU7 by an image signal.

The light guide 17 is subjected to a grind processing such that the irradiating surface 17a of the introduced illumination light is positioned in the same plane as the distal end surface of the distal end portion 2, and inserted in through the insertion portion 3 up to the light guide connector portion 5 of the grasping portion 4 shown in FIG. 1. The light guide 17 is further connected to the connector portion 12 of the light guide cable 11 to introduce the illumination light from the light source apparatus 10.

The glass surface portion 15a of the cover glass 15 and the distal end surface 16a of the optical member holding tube 16 of the present embodiment are subjected to a hydrophilic processing by, for example, a transparent thin-film photocatalyst such as titanium oxide, so that a first hydrophilic portion 20 is film-formed in the regions of the glass surface portion 15a and the distal end surface 16a.

Here, using FIG. 4, hydrophilicity of the present embodiment is defined below.

As shown in FIG. 4, in general, a contact angle θ with a member surface adhered with a liquid 25 having a water drop shape, which is greater than 80 degrees (θ>80 degrees), e.g., because the member surface is processed with an ion wax, Teflon (a registered trademark), etc., is regarded as water repellent; the contact angle θ which is approximately 50 degrees (θ≑50 degrees) as unprocessed; and the contact angle θ which is smaller than 20 degrees (θ<20 degrees) because of the below-described processing, as hydrophilic.

The rigid endoscope 1 of the present embodiment includes the first hydrophilic portion 20 having the glass surface portion 15a of the cover glass 15 and the distal end surface 16a of the optical member holding tube 16 subjected to the defogging processing of the hydrophilic processing. Thus, the rigid endoscope 1 is configured such that, even if the distal end portion 2 is adhered with the liquid 25 such as a body fluid, a water drop resulting from steam, a physiological saline solution, etc., the liquid adhering on the cover glass 15 imposes no adverse effect on the image pickup light condensed by the image pickup device unit 18a via the cover glass 15 and the optical lens group 18 to obtain an endoscope image.

The contact angle θ preferable for the first hydrophilic portion 20 is not greater than 10 degrees (θ≦10 degrees) of the above-defined hydrophilicity. More preferably, the first hydrophilic portion 20 is in a super hydrophilic state such that a water drop adhering on the surfaces of the glass surface portion 15a and the distal end surface 16a has a contact angle θ not greater than 5 degrees (θ≦5 degrees). Moreover, the first hydrophilic portion 20 has an enough tolerance for autoclave processing which is a high temperature-high pressure steam sterilization processing performed in cleaning sterilization of the rigid endoscope 1.

Returning to FIG. 3, the rigid endoscope 1 constructed as above prevents fogging by means of the first hydrophilic portion 20, and causes a fluid 26 adhering on the distal end surface of the distal end portion 2 to turn into a conformed state without becoming a water drop on the glass surface portion 15a and the distal end surface 16a. The fluid 26 becomes a water drop swelled by surface tension on the distal end surface 2a of the distal end portion 2 not subjected to hydrophilic processing. Note that FIG. 3 shows a state where a bigger water drop 26a is produced on the distal end surface 2a on a lower part side of the distal end portion 2 by gravity, assuming that up/down direction as viewed toward the paper surface is identical with the vertical up/down direction.

That is, the rigid endoscope 1 of the present embodiment can prevent fogging by hydrophilic processing on the distal end surface 16a and the glass surface portion 15a, and especially prevent production of water drops by fluids such as body fluid, steam and physiological saline solution in the abdominal cavity, on the glass surface portion 15a. Therefore, no water drops are produced in the light path of the image pickup light incident into the image pickup device unit 18a via the optical lens group 18 from the cover glass 15. Accordingly, the rigid endoscope 1 can eliminate a bad influence on the image captured of the inside of the abdominal cavity by distortion due to fog and water drops, etc., thus obtaining a clear endoscope image.

The above-mentioned effect can be achieved more surely by performing the hydrophilic film-forming processing on the entire area of the distal end surface and a circumferential side surface of the distal end portion 2 of the rigid endoscope 1 as described below.

Specifically, as shown in FIGS. 5 and 6, the rigid endoscope 1 includes, in addition to the above-mentioned first hydrophilic portion 20, a second hydrophilic portion 21 which is film-formed, including the irradiating surface 17a of the light guide 17 and the circular ring-shaped distal end surface 2a of the distal end portion 2 that are subjected to a defogging processing with a hydrophilic film.

The second hydrophilic portion 21 is a hydrophilic film continuous with the first hydrophilic portion 20 at a boundary portion between the distal end surface 16a of the optical member holding tube 16 and the irradiating surface of the light guide 17. The second hydrophilic portion also has an enough tolerance for the autoclave processing as the first hydrophilic portion 20, and is a hydrophilic film that is subjected to a super hydrophilic processing such that a contact angle of a fluid 26 on the irradiating surface 17a and the distal end surface 2a that are super hydrophilic is not greater than 5 degrees (θ≦5 degrees).

Thus, by the rigid endoscope 1 having the second hydrophilic portion 21 film-formed, the fluid 26 adhering on the distal end surface of the distal end portion 2, including the glass surface portion 15a, the distal end surface 16a, the irradiating surface 17a, and the distal end surface 2a, turns into a conformed state, without becoming a water drop, as shown in FIG. 6. On the circumferential side surface of the distal end portion 2 not subjected to hydrophilic processing, the fluid 26 becomes a water drop swelled by surface tension. Here, FIG. 6 shows a state where the water drop 26a is produced on the circumferential side surface of the distal end portion 2 by gravity, also assuming that up/down direction as viewed toward the paper surface is identical with the vertical up/down direction.

That is, by providing the second hydrophilic portion 21 to the rigid endoscope 1 that a large view angle such as, e.g., 170 degrees is set, it is prevented that water drops are produced on the entirety of the distal end surface of the distal end portion 2 and enter the view angle, which enables obtaining a good endoscope image.

Note that, to prevent fogging and water drops from being produced in the light path of the image pickup light incident from the cover glass 15, the rigid endoscope 1 having the second hydrophilic portion 21 that is film-formed as above may be configured such that the first hydrophilic portion 20 is subjected to the super hydrophilic processing and the second hydrophilic portion 21 has a hydrophilic characteristic with a contact angle θ not greater than 20 degrees (θ<20 degrees) which is sufficient to prevent general production of water drops, as mentioned above.

Furthermore, as shown in FIGS. 7 and 8, also on a circumferential side surface of the distal end portion 2 of the rigid endoscope 1, a third hydrophilic portion 22 is film-formed that is subjected to the defogging processing with a hydrophilic film. The third hydrophilic portion has an enough tolerance for the autoclave processing as the first and second hydrophilic portions 20, 21. The third hydrophilic portion 22 is film-formed on the distal end portion 2 to be a hydrophilic film continuous with the second hydrophilic portion 21. In other words, the first to third hydrophilic portions 20 to 22 are here film-formed over the entirety of the distal end portion 2 to be continuous without a gap.

The third hydrophilic portion 22 may be a hydrophilic film subjected to a super hydrophilic processing such that the contact angle of the fluid 26 on the irradiating surface 17a and the distal end surface 2a that are super hydrophilic is not greater than 5 degrees (θ≦5 degrees). Nonetheless, it suffices to form a film on the circumferential side surface of the distal end portion 2 such that, for example, the contact angle θ becomes not greater than 30 degrees, instead of the contact angle θ not greater than 20 degrees (θ<20 degrees) defined as hydrophilic above.

That is, for the rigid endoscope 1 to prevent production of fogging and water drops to obtain a clear endoscope image, the smaller the contact angle θ of the fluid 26 on the glass surface portion 15a and on the distal end surface 16a of the first hydrophilic portion 20, the more preferable. On the other hand, the rigid endoscope 1 does not need much of the effect to prevent production of fogging and water drops on the circumferential side surface of the distal end portion 2. Therefore, the contact angle θ of the fluid 26 on the circumferential side surface of the distal end portion 2 where the third hydrophilic portion 22 is film-formed may be set to be somewhat large.

Here, the third hydrophilic portion 22 is film-formed on the entirety of the outer circumference portion of the distal end portion 2. Yet, a length L in the axial direction of a range of the outer circumferential surface of the distal end portion 2 where the third hydrophilic portion 22 is film-formed may be about 3 cm from the distal end surface 2a toward a proximal end side.

Moreover, not only on the distal end portion 2 of the rigid endoscope 1, but also on an outer surface of the insertion portion 3, a fourth hydrophilic film may be formed that is similar to each of the hydrophilic portions 20 to 22. That is, the rigid endoscope 1 has the hydrophilic films formed both on the distal end portion 2 and the insertion portion 3. Thus, a fluid coming into contact with the outer circumferential surface evenly spreads to improve insertability into the abdominal cavity.

Note that each of the above-mentioned effects can be also achieved by using a hydrophilic cap 30 which is a hydrophilic cap subjected to the defogging processing with a hydrophilic film and attachable to/detachable from the distal end portion 2 of the rigid endoscope 1, as shown in FIGS. 9 and 10. To describe in detail, the hydrophilic cap 30 includes a cylindrical body 31 with an essentially circular ring shape having a length that can cover the entirety of the outer circumference portion of the distal end portion 2 having elasticity, and a plate member 32 that is transparent and having a disc shape at a distal end of the cylindrical body 31.

The hydrophilic cap 30 has the defogging processing with a hydrophilic film performed at least on distal end surfaces of the hydrophilic cap 30, i.e., a surface portion 32a of the plate member 32 and a distal end surface 31a of the cylindrical body 31. In the present embodiment, a circumferential side surface of the cylindrical body 31 is also subjected to the defogging processing with a hydrophilic film. The hydrophilic cap 30 is prevented from falling off from the distal end portion 2 when attached on the distal end portion 2, by elastic deformation of the cylindrical body 31. Note that screw grooves may be formed on the outer circumferential surface of the distal end portion 2 and on an inner circumferential surface of the cylindrical body 31 of the hydrophilic cap 30 to enable the hydrophilic cap 30 to be detachably attached to the distal end portion 2.

The hydrophilic cap 30 configured as above prevents the fluid 26 on the outer surface subjected to the hydrophilic processing from becoming water drops, and turns the water drops into a conformed state on the outer surface, as each of the hydrophilic portions 20 to 22. In other words, the hydrophilic cap 30 has a hydrophilic film same as the above-mentioned first hydrophilic portion 20 formed on the surface portion 32a of the plate member 32 and the distal end surface 31a of the cylindrical body 31, and also has a hydrophilic film same as the above-mentioned third hydrophilic portion 22 continuously formed on the outer circumference portion of the cylindrical body 31.

Thus, the rigid endoscope 1 can constantly obtain a clear endoscope image by simply changing the hydrophilic cap 30 as the hydrophilic effect deteriorates.

Next, hydrophilic processing to form the first to third hydrophilic portions 20 to 22 is described.

Each of the hydrophilic portions 20 to 22 of the present embodiment is subjected to the hydrophilic processing by film-forming, by the sputtering method, a film of a photocatalyst such as, e.g., titanium oxide on each of the glass surface portion 15a of the cover glass 15, the distal end surface 16a of the optical member holding tube 16, the irradiating surface 17a of the light guide 17, and the distal end surface 2a and the outer circumferential surface of the distal end portion 2. The outer surface of the hydrophilic cap 30 is also processed in a similar manner. So as not to obstruct incidence of the photographing light, a transparent thin-film photocatalyst is used for at least the glass surface portion 15a of the cover glass 15 where the first hydrophilic portion 20 is film-formed.

Note that each of the hydrophilic portions 20 to 22 is not to be limitatively subjected to the above-mentioned hydrophilic processing of forming a transparent thin-film photocatalyst such as of the titanium oxide by the sputtering method, but may be subjected to a film-forming processing by a gas-phase method such as the sputtering method and the evaporation methods, liquid-phase methods such as dipping coating and spin coating, a method of applying a medicament that serves as the basis of the hydrophilic film with a cloth, absorbent cotton, etc., so as to form, e.g., a thin film of various coating agents having light transparency to subject each of the above-mentioned surfaces to a hydrophilic processing.

Furthermore, the above-mentioned surfaces may be processed with hydrophilic films to serve as the first to third hydrophilic portions 20 to 22 by forming a petaloid alumina film having a minute uneven surface with surface roughness of, e.g., Rz=50 nm-130 nm by the Sol-Gel method.

Medicaments to serve as the hydrophilic film include a surfactant for defogging. By applying this surfactant, each of the hydrophilic portions 20 to 22 is film-formed. Some of the surfactants for defogging form a hydrophilic film, main ingredients of which are, e.g., liquid or solid cationic surfactant, anionic surfactant, non-ionic surfactant, ampho-ionic surfactant, etc.

Examples of cationic surfactant include alkyl trimethyl ammonium salt, dialkyl dimethyl ammonium chloride, alkyl pyridinium chloride, etc. Examples of anionic surfactant include fat acid salt, alpha.-sulfo-fatty acid ester salt, alkyl-sulfuric acid triethanolamine, etc. Examples of non-ionic surfactant include fatty acid diethanolamides, polyoxyethylene alkyl ether, polyoxyethylene alkyl phenyl ether, etc. Examples of ampho-ionic surfactant include alkyl carboxy betaine, etc. Note that these surfactants are not limited to the above-listed components, and are sufficed to have biocompatibility. Furthermore, each of the above-mentioned surfactants for developing the hydrophilic characteristic may contain an additive such as, e.g., alcohol, glycerol to facilitate application on the glass surface portion 15a and the distal end surface 16a and to even the hydrophilic film of the surfactant.

Note that, in assembling the rigid endoscope 1, members thereof may be separately subjected to the hydrophilic film-forming processing to be thereafter assembled together so as to film-form the first to third hydrophilic portions 20 to 22. Alternatively, the members may be assembled in advance to have thereon the first to third hydrophilic portions 20 to 22 film-formed. The latter way of assembling can surely form a hydrophilic film also at a border part between the members, thereby allowing more surely improving the hydrophilic effect, obtaining high effects of defogging and preventing water drop production.

Incidentally, when film-forming each of the hydrophilic portions 20 to 22, the above-mentioned gas-phase method such as the sputtering method or the evaporation method can form a hydrophilic film with constant quality and good reproducibility, once a film-forming condition is determined. The gas-phase method can form a film over a comparatively wide range, permitting continuously and jointlessly forming a hydrophilic film at the border portions of the members, which enables obtaining high effects of defogging and preventing water drop production.

The liquid-phase method such as dipping coating and spin coating can form a hydrophilic film without requiring expensive equipment, as compared to the above-mentioned gas-phase method. Moreover, the liquid-phase method can comparatively easily adjust thickness and quality of the hydrophilic film. For this reason, the liquid-phase method has an advantage of enabling to ensure the quality of the hydrophilic film, minimizing production cost.

The method of forming a hydrophilic film by applying surfactant with a cloth or absorbent cotton can be significantly inexpensive compared to the gas-phase method and the liquid-phase method and allows the user to freely conduct the application, which leads to an advantage of providing good usability.

In each of the above-mentioned methods of forming a hydrophilic film, for example, each of the first to third hydrophilic portions 20 to 22 can be film-formed at the same time after assembling the members of the rigid endoscope 1, thus allowing forming a film continuously and jointlessly at each of the border parts of the first to third hydrophilic portions 20 to 22. Accordingly, the rigid endoscope 1 easily have a water screen spread on each of the hydrophilic portions 20 to 22 even in a comparatively high humidity, leading to superior configuration for the effects of defogging and preventing water drop production, which enables obtaining a better endoscope image.

In the case of separately film-forming the first to third hydrophilic portions 20 to 22 on the members before assembling the rigid endoscope 1, on the first hydrophilic portion 20 can be formed a high performance hydrophilic film by the gas-phase method such as the sputtering method and the evaporation method or by the liquid-phase method such as dipping coating and spin coating, while on the second and third hydrophilic portions 21, 22 can be formed a film inexpensively by the above-mentioned liquid-phase method or a method using a surfactant. That is, on the first hydrophilic portion 20 having a direct influence on the photographing light, there is formed a hydrophilic film with high hydrophilic characteristic such as super hydrophilic characteristic. On the second and third hydrophilic portions 21, 22 having less direct influence on the photographing light, a hydrophilic film with somewhat lower hydrophilic characteristic is formed. Accordingly, separate use of the film characteristics is enabled.

Furthermore, the above-mentioned method does not require large equipment to perform the gas-phase method such as the sputtering method and the evaporation method which is adapted to the size of the rigid endoscope 1 assembled, but permits a normal sputtering apparatus or evaporation apparatus to form a film on the cover glass 15 and the optical member holding tube 16, serving as respective members of the glass surface portion 11a and the distal end surface 16a, on which the first hydrophilic portion 20 is film-formed.

Incidentally, the above-mentioned present embodiment, which refers to the rigid endoscope 1 having the hydrophilic portions 20 to 22 which is to be inserted in the abdominal cavity, can also be applied to a flexible endoscope to be inserted into a body cavity such as the large intestine.

Referring here to FIGS. 11 to 14, a flexible endoscope system 200 including a flexible endoscope 40 is briefly described.

As shown in FIG. 11, the flexible endoscope system 200 includes the flexible endoscope 40, and the monitor 6, the CCU7, and the light source apparatus 10 that are mentioned above.

The flexible endoscope 40 includes: an insertion portion 44 to be inserted in the body cavity, comprised of a distal end portion 41, a bending portion 42, and a flexible tube portion 43; and an operation portion 45 provided in a linked manner to a proximal end of the insertion portion 44. From the operation portion 45 extends a universal cord 45a having a connector portion 45b to be connected to the light source apparatus 10.

As shown in FIG. 12, on a distal end surface 41a of the distal end portion 41 of the flexible endoscope 40, there are disposed: an observation window 51 as an optical member through which photographing light transmits to internal observation means not shown such as CCD or CMOS; two illumination windows 52, 53 to irradiate illumination light; an aperture portion of a treatment instrument channel 54 configuring an endoscope conduit; and a nozzle 55 to spray a fluid on the observation window 51.

As shown in FIG. 12, the flexible endoscope 40 of the present embodiment has a first hydrophilic portion 47 film-formed on the observation window 51 on the distal end surface 41a and on a periphery portion 51a of the observation window 51, as the above-mentioned rigid endoscope 1. The first hydrophilic portion 47 of the flexible endoscope 40 is equivalent to the first hydrophilic portion 20 of the rigid endoscope 1 shown in FIGS. 2 and 3, and achieves the same effect.

The flexible endoscope 40 may further include, in addition to the first hydrophilic portion 47, a second hydrophilic portion 48 that is film-formed on the entire area of the distal end surface 41a as shown in FIG. 13. The first hydrophilic portion 47 and the second hydrophilic portion 48 of the flexible endoscope 40 are equivalent to the first hydrophilic portion 20 and the second hydrophilic portion 21 of the rigid endoscope 1 shown in FIGS. 5 and 6, and achieve the same effect.

The flexible endoscope 40 may furthermore include, in addition to the first and second hydrophilic portions 47, 48, a third hydrophilic portion 49 that is film-formed on an outer circumferential surface of the distal end portion 41 as shown in FIG. 14. The first to third hydrophilic portions 47, 48, 49 of the flexible endoscope 40 are equivalent to the first to third hydrophilic portions 20, 21, 22 of the rigid endoscope 1 shown in FIGS. 7 and 8, and achieve the same effect.

Second Embodiment

Next, a second embodiment of the present invention is described.

Figure 15:
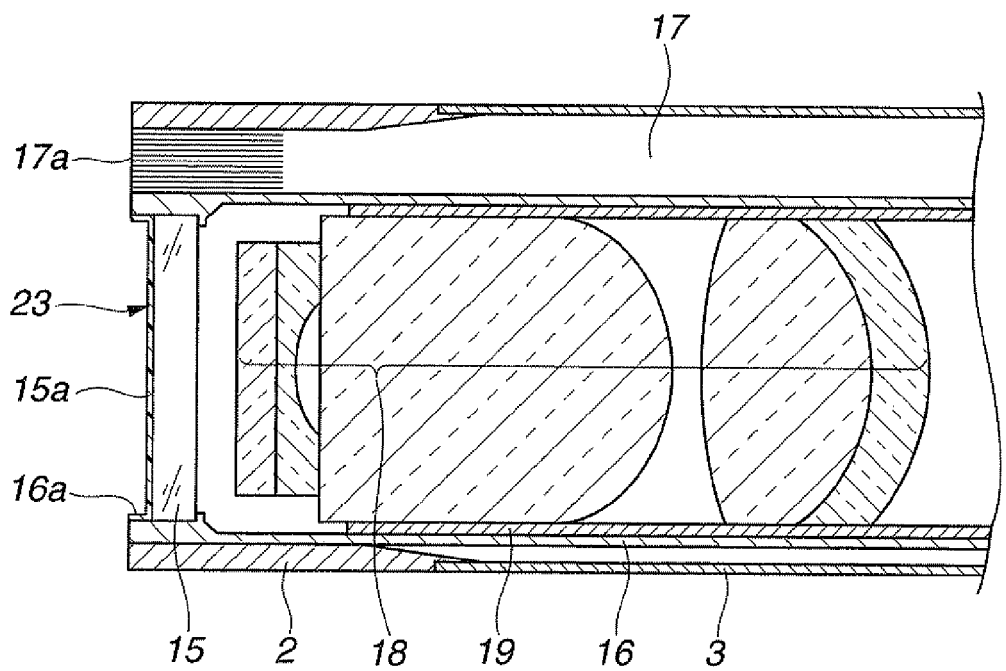
FIG. 15 relates to a second embodiment, and is a sectional view of a distal end part of a rigid endoscope.
Figure 16:
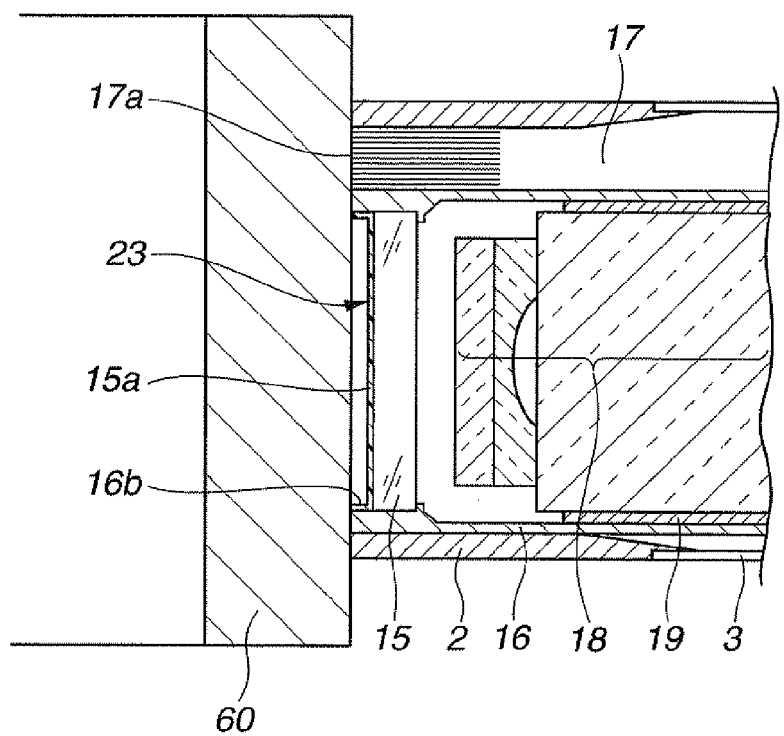
FIG. 16 relates to the second embodiment, and is a sectional view showing a state of grinding a light guide irradiating surface of the rigid endoscope of FIG. 15.
Figure 17:
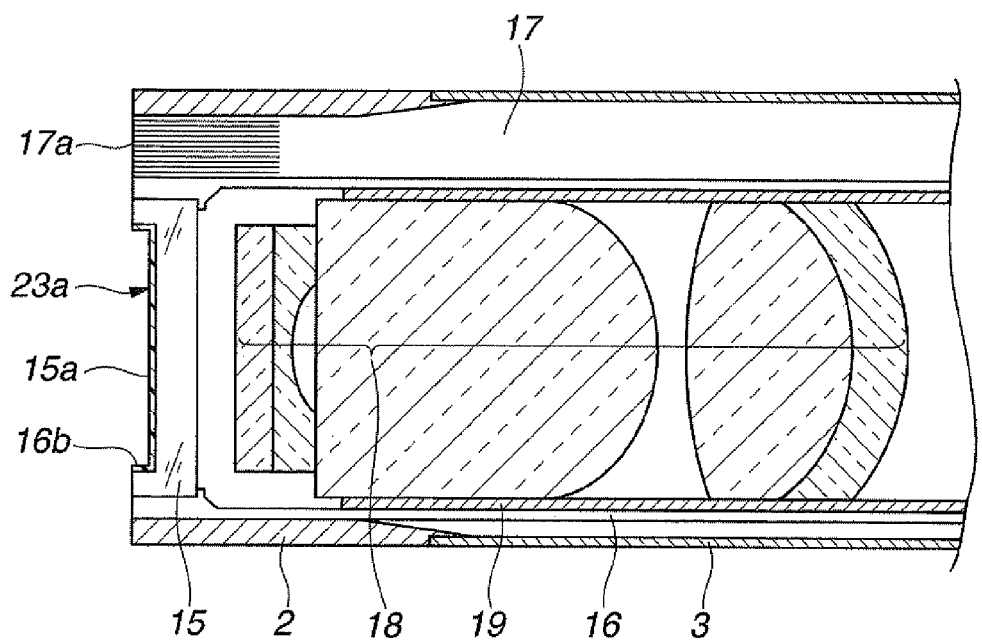
FIG. 17 relates to the second embodiment, and is a sectional view of a distal end part of a rigid endoscope in a modification example.
Figure 18:
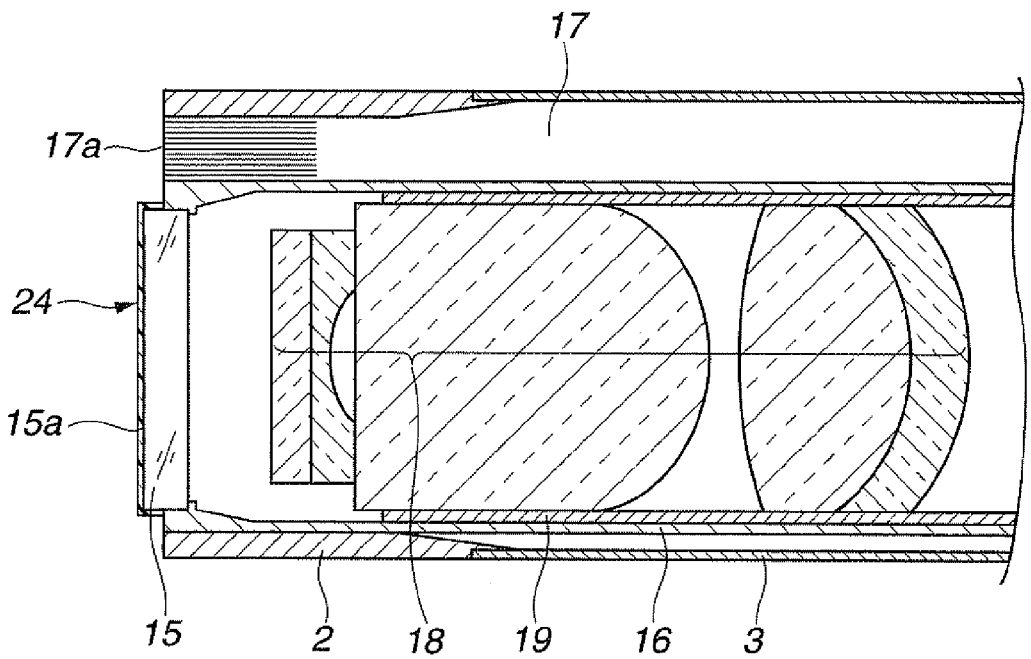
FIG. 18 relates to the second embodiment, and is a sectional view of the distal end part of the rigid endoscope.
Figure 19:
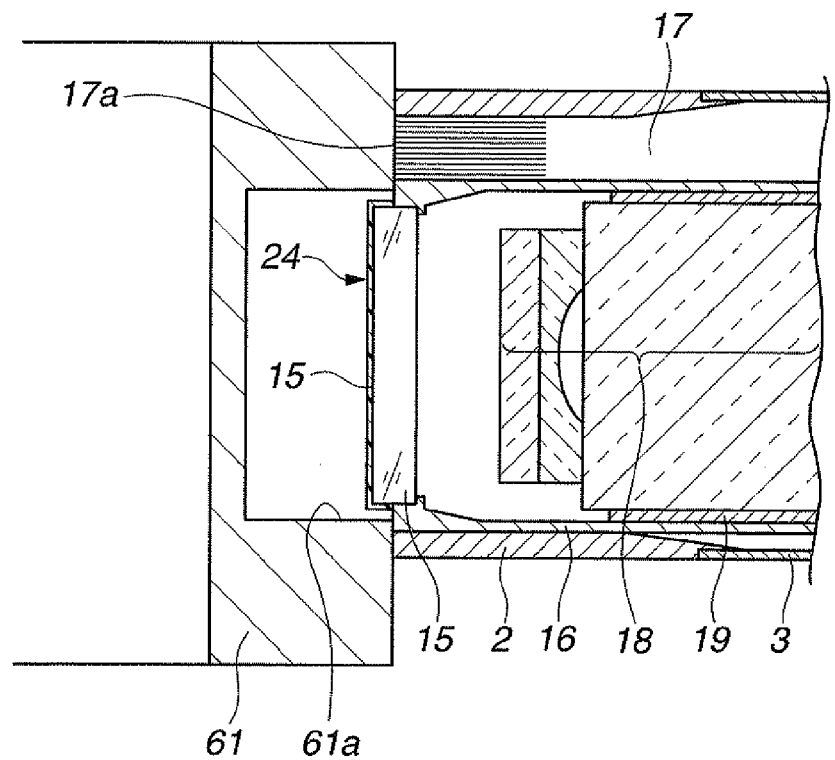
FIG. 19 relates to the second embodiment, and is a sectional view showing a state of grinding a light guide irradiating surface of the rigid endoscope of FIG. 18.

FIGS. 15 to 19 relate to the second embodiment. FIG. 15 is a sectional view of a distal end part of a rigid endoscope. FIG. 16 is a sectional view showing a state of grinding a light guide irradiating surface of the rigid endoscope of FIG. 15. FIG. 17 is a sectional view of a distal end part of a rigid endoscope in a modification example. FIG. 18 is a sectional view of the distal end part of the rigid endoscope. FIG. 19 is a sectional view showing a state of grinding a light guide irradiating surface of the rigid endoscope of FIG. 18.

Note that, in the description of the present embodiment, the same components as in the first embodiment use the same symbols, and descriptions thereof are omitted.

Incidentally, production of the general rigid endoscope 1 includes a grind processing to grind and surface-trim the light guide 17 protruded from the distal end surface of the distal end portion 2 and solder or wax used as fixing means to install the cover glass 15 to the optical member holding tube 16.

The light guide 17, which is configured of a fibrous fiber member, is ground to form the irradiating surface 17a on the distal end surface of the distal end portion 2.

On the other hand, a fixing solder or wax is used especially when installing the cover glass 15 to the optical member holding tube 16. The solder or wax is for air-tightly/liquid-tightly maintaining the inside of the insertion portion 3, where the observation means such as the optical lens group 18 and the relay lenses are disposed, with respect to the outside, and for ensuring resistibility to disinfection and sterilization. The soldering or waxing processes are manually performed. Because the solder or wax excludes a wipe-off process which is allowed for adhesive, it is necessary to grind the part of the solder or wax protruded from the distal end surface.

In view of the above, the present embodiment is configured as described below to prevent especially the first hydrophilic portion 20 that is film-formed on the cover glass 15 from being exfoliated by the grinding process. Note that the present embodiment is made valid if the grinding process is performed after the cover glass 15, on which a hydrophilic portion 23 which is a hydrophilic film as a defogging coating is film-formed, is installed in advance to the optical member holding tube 16.

To describe in detail, as shown in FIG. 15, the rigid endoscope 1 of the present embodiment has the glass surface portion 11a of the cover glass 15 fixed shifted rearward by about 0.1 mm to 0.5 mm from the distal end surface 16a of the optical member holding tube 16 disposed in the distal end portion 2. Note that the optical member holding tube 16 may have a hydrophilic film formed also on an inner circumferential surface 16b that extends from a distal end surface 16a of the optical member holding tube 16 to the glass surface portion 15a of the cover glass 15.

Such configuration enables grounding the distal end surface of the distal end portion 2 of the rigid endoscope 1 without the hydrophilic portion 23 of the glass surface portion 15a of the cover glass 15 being exfoliated by an grinding tool 60, as shown in FIG. 16. As a result, the hydrophilic portion 23 can maintain an effective hydrophilic characteristic.

Note that, as shown in FIG. 17, the cover glass 15 may have a concave portion 15b including the glass surface portion 15a formed therein, and a hydrophilic portion 23a of a hydrophilic film as a defogging coating may be film-formed on a concave surface of the concave portion 15b. In other words, the cover glass 15 is configured to prevent the concave surface of the concave portion 15b from being ground, and the hydrophilic portion 23a exfoliated, during a grinding process.

Moreover, as shown in FIG. 18, the cover glass 15, on which the hydrophilic portion 24 of the hydrophilic film as a defogging coating is film-formed, may be disposed to the optical member holding tube 16 so as to be convex on the distal end surface of the rigid endoscope 1. Such configuration of the rigid endoscope 1 enables grinding, while trimming, especially the irradiating surface 17a of the light guide 17 without exfoliating the hydrophilic portion 24 of the cover glass 15 by a grinding tool 61 with a concave portion 61a formed therein, as shown in FIG. 19.

Note that the grinding tool 61 is configured to be cocentered with the cover glass 15 to rotate to grind the same, with the center of the concave portion 61a agreeing with the center of the cover glass 15.

Third Embodiment

Next, a third embodiment of the present invention is described.

Figure 20:
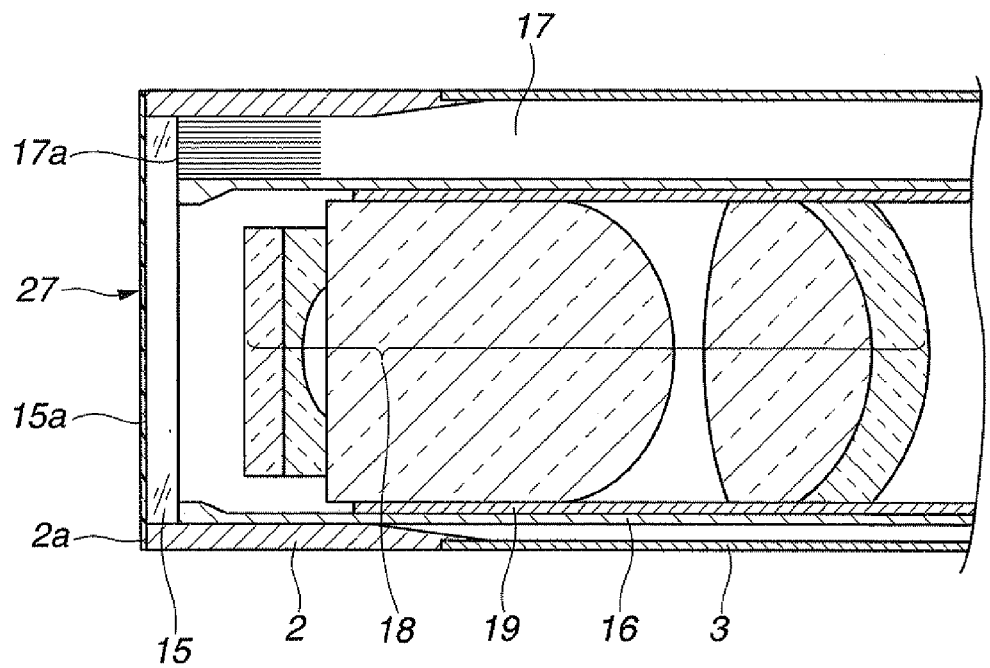
FIG. 20 relates to a third embodiment, and is a sectional view showing a distal end part of a rigid endoscope.
Figure 21:
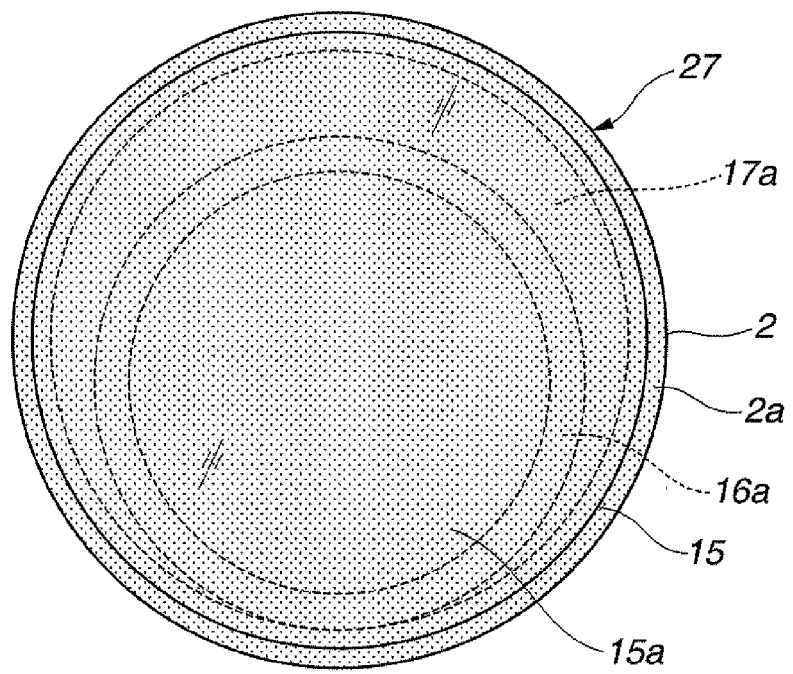
FIG. 21 relates to the third embodiment, and is a plan view showing a distal end surface of the rigid endoscope.
Figure 22:
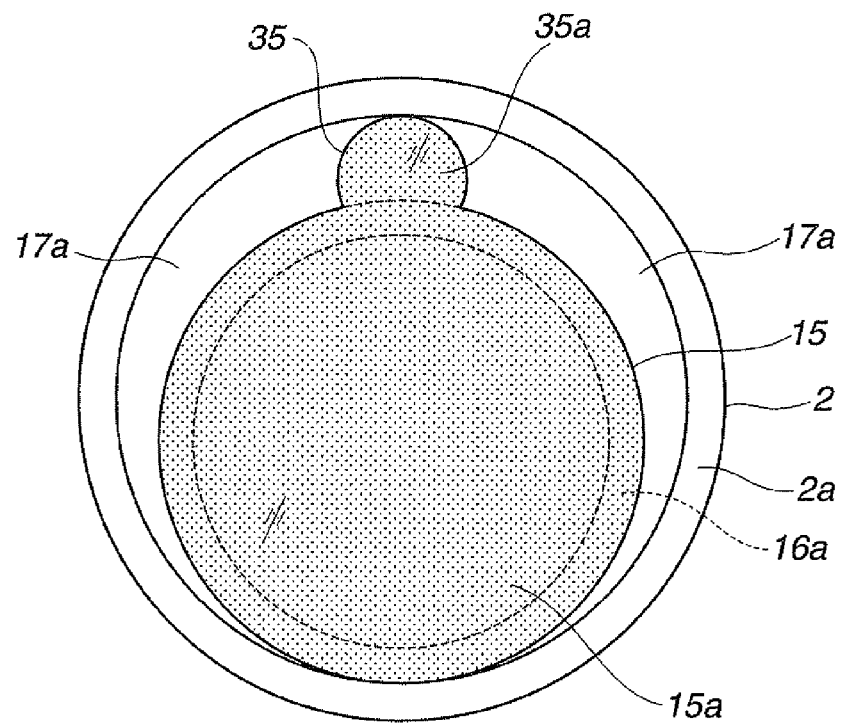
FIG. 22 relates to the third embodiment, and is a plan view showing a distal end surface of a rigid endoscope shown in a modification example.
Figure 23:
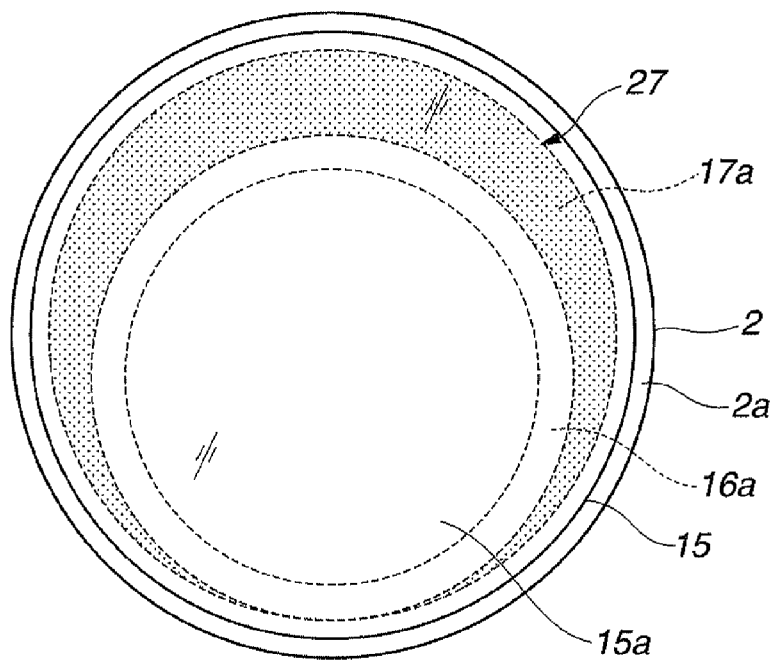
FIG. 23 relates to the third embodiment, and is a plan view showing the distal end surface of the rigid endoscope to illustrate heat conversion means.
Figure 24:
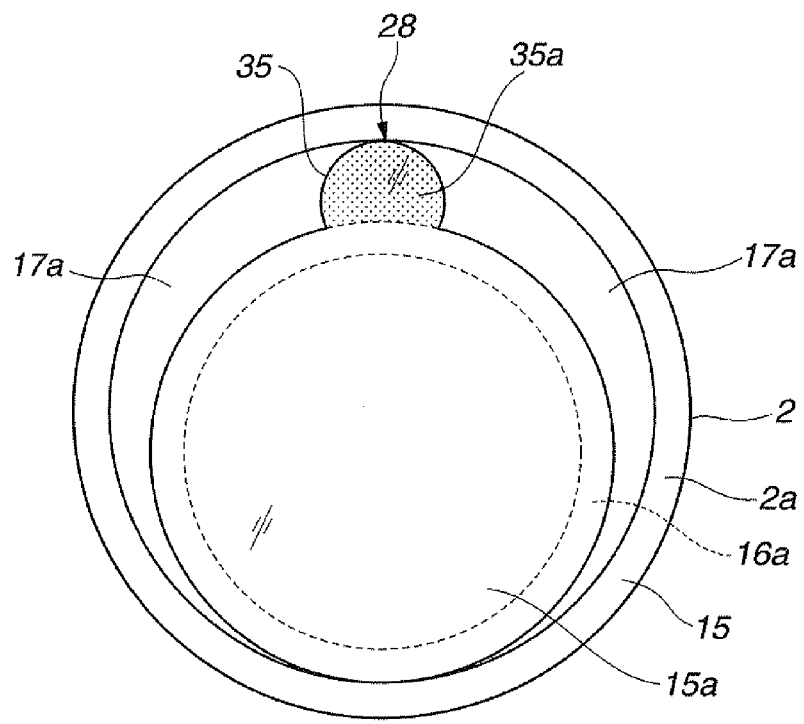
FIG. 24 relates to the third embodiment, and is a plan view shown in a modification example, showing the distal end surface of the rigid endoscope to illustrate the heat conversion means.
Figure 25:
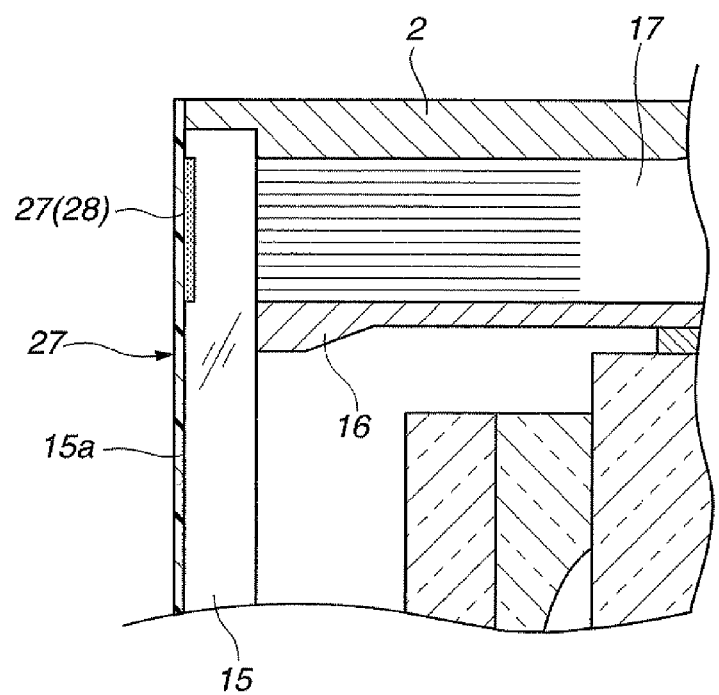
FIG. 25 relates to the third embodiment, and is a partial sectional view showing the distal end part of the rigid endoscope to illustrate the heat conversion means.
Figure 26:
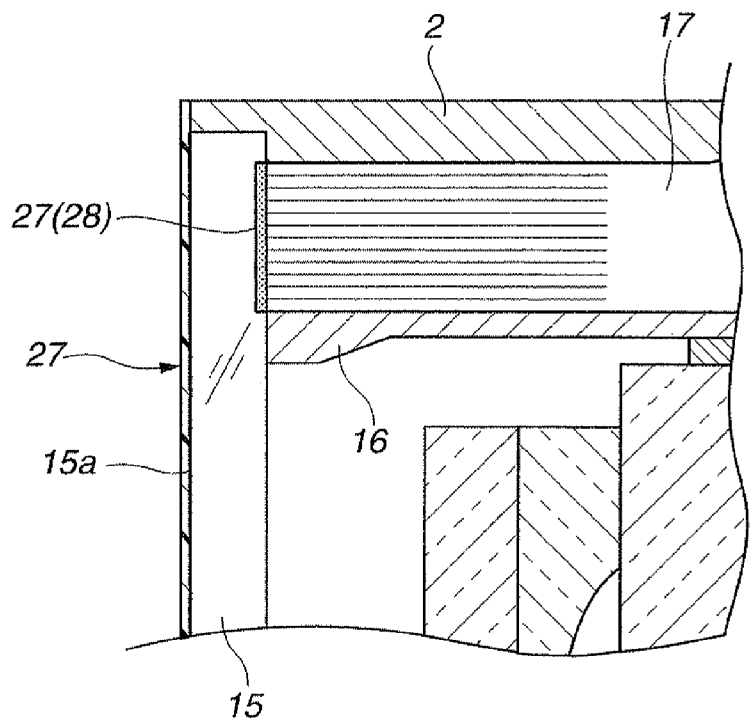
FIG. 26 relates to the third embodiment, and is a partial sectional view shown in a modification example, showing the distal end part of the rigid endoscope to illustrate heat conversion means.
Figure 27:
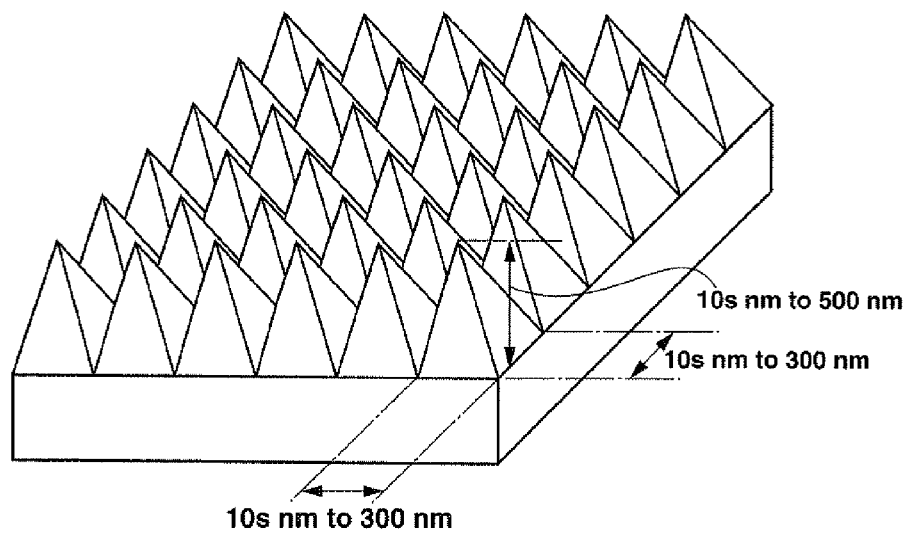
FIG. 27 relates to the third embodiment, and is a view to illustrate a minute uneven structure having an antireflection effect.
Figure 28:
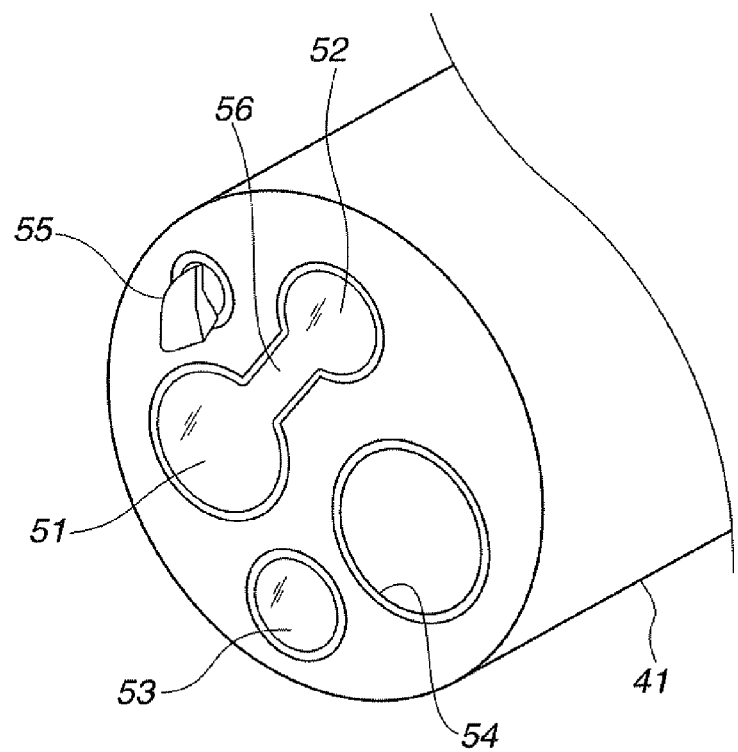
FIG. 28 relates to the third embodiment, and is a perspective view showing the distal end part of the flexible endoscope.
Figure 29:
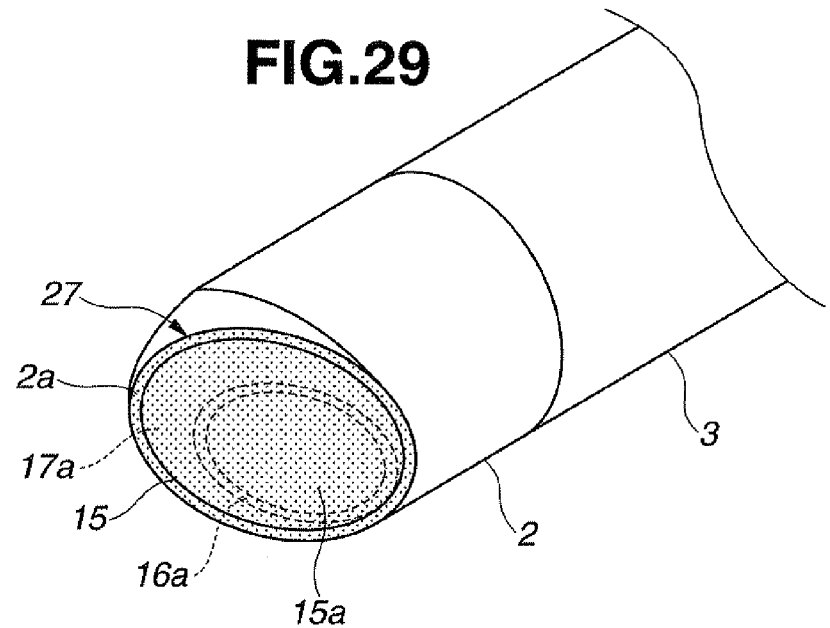
FIG. 29 relates to the third embodiment, and is a perspective view of the distal end part of the rigid endoscope showing an exemplary measure to prevent flare caused by illumination light.
Figure 30:
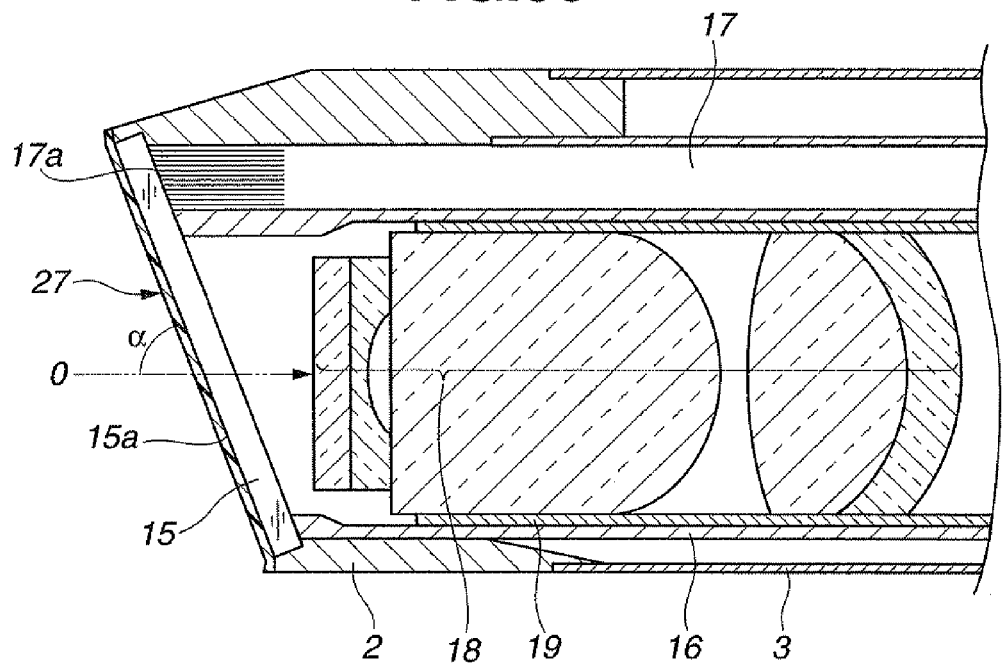
FIG. 30 relates to the third embodiment, and is a sectional view of the distal end part of the rigid endoscope of FIG. 29.
Figure 31:
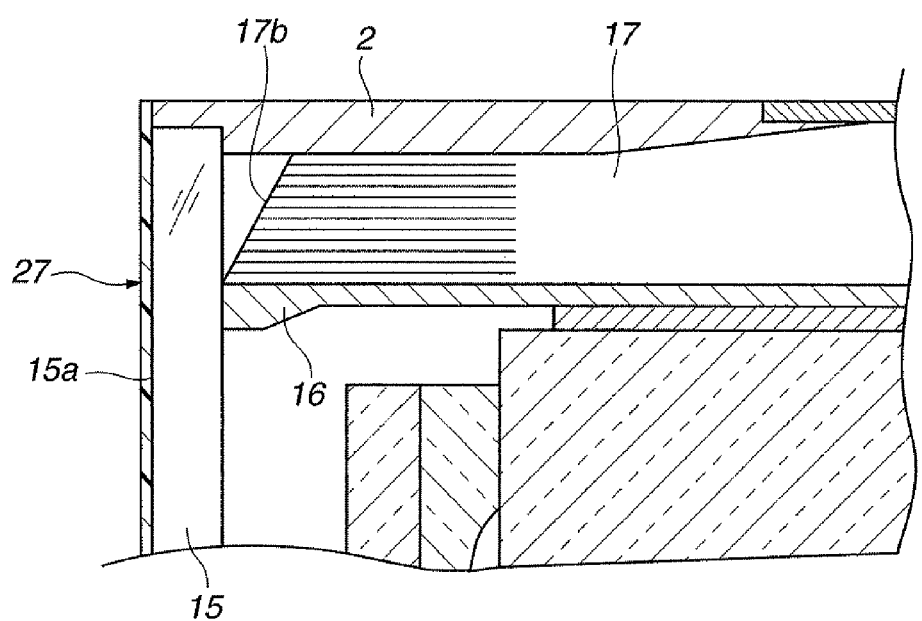
FIG. 31 relates to the third embodiment, and is a partial sectional view of the distal end part of the rigid endoscope showing a modification example of the measure to prevent flare caused by illumination light.
Figure 32:
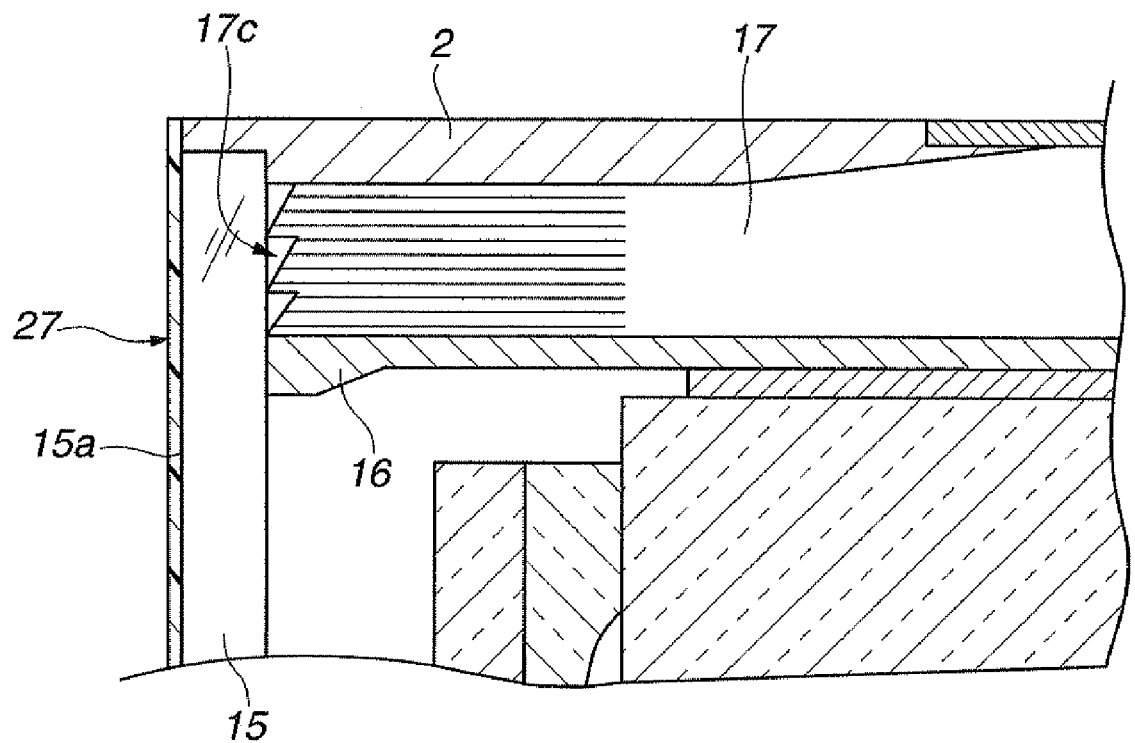
FIG. 32 relates to the third embodiment, and is a partial sectional view of the distal end part of the rigid endoscope showing a modification example of the measure to prevent flare caused by illumination light.

FIGS. 20 to 32 relate to a third embodiment. FIG. 20 is a sectional view showing a distal end part of a rigid endoscope. FIG. 21 is a plan view showing a distal end surface of the rigid endoscope. FIG. 22 is a plan view showing a distal end surface of a rigid endoscope shown in a modification example. FIG. 23 is a plan view showing the distal end surface of the rigid endoscope to illustrate heat conversion means. FIG. 24 is a plan view shown in a modification example, showing the distal end surface of the rigid endoscope to illustrate the heat conversion means. FIG. 25 is a partial sectional view showing the distal end part of the rigid endoscope to illustrate the heat conversion means. FIG. 26 is a partial sectional view shown in a modification example, showing the distal end part of the rigid endoscope to illustrate the heat conversion means. FIG. 27 is a view showing to illustrate a minute uneven structure having an antireflection effect. FIG. 28 is a perspective view showing the distal end part of the flexible endoscope. FIG. 29 is a perspective view of the distal end part of the rigid endoscope showing an exemplary measure to prevent flare caused by illumination light. FIG. 30 is a sectional view of the distal end part of the rigid endoscope of FIG. 29. FIGS. 31 and 32 are each a partial sectional view of the distal end part of the rigid endoscope showing a modification example of the measure to prevent flare caused by illumination light.

Note that, in the description of the present embodiment, for components same as in the above-mentioned embodiments, the same symbols are used, and descriptions thereof are omitted.

As shown in FIG. 20, the rigid endoscope 1 of the present embodiment is so configured that the cover glass 15 is held by the distal end portion 2. As shown in FIG. 21, the cover glass 15 has a shape to essentially cover the distal end surface of the rigid endoscope 1, and is so disposed that the distal end surface 2a and the glass surface portion 15a of the distal end portion 2 are positioned in the same plane.

On the glass surface portion 15a of the cover glass 15, there is film-formed a hydrophilic portion 27 of a hydrophilic film as a defogging coating, continuous with the distal end surface 2a of the distal end portion 2. Note that the irradiating surface 17a of the light guide 17 is in contact with a rear surface of the cover glass 15.

With the rigid endoscope 1 of the present embodiment thus configured, the illumination light from the irradiating surface 17a of the light guide 17 warms a rear surface portion of the cover glass 15 that is in contact with the irradiating surface 17a. The heat by the illumination light of the light guide 17 conducts and spreads over the entirety of the cover glass 15, thus preventing moisture condensation due to temperature difference between inner abdominal cavity and the outside.

As a result, the rigid endoscope 1 of the present embodiment can achieve the effects of the above-mentioned first embodiment, i.e., the defogging and hydrophilic effects by the hydrophilic portion 27, as well as prevent production of water drops in the light path of the image pickup light from the cover glass 15 through the optical lens group 18 and the relay lens group to be incident into the image pickup device unit in the camera head 9, thus obtaining a clearer endoscope image without a photographed image of the inner abdominal cavity influenced by distortion due to fogging, water drops, etc.

Note that, as shown in FIG. 22, the cover glass 15 may include a protruding portion 35 protruding from a part of the outer circumference portion of the cover glass 15 and having a surface portion 35a in the same plane as the glass surface portion 15a. The protruding portion 35 has here, an essentially arc-shaped outer circumference, which overlaps a part of the irradiating surface 17a of the light guide 17 to be heated by transmission of the illumination light. The protruding portion 35 conducts an amount of heat from the illumination light to the cover glass 15 to allow sufficiently preventing moisture condensation.

In other words, the protruding portion 35 has an area that is irradiated with an amount of illumination light that allows an enough heating to prevent moisture condensation on the cover glass 15. As a result, the rigid endoscope 1 can achieve the above-mentioned effects even if the cover glass 15 is shaped including the protruding portion 35.

Note that structures to efficiently convert the illumination light from the light guide 17 to heat may include one where a part of the cover glass 15 or the protruding portion 35 overlapped with the irradiating surface 17a of the light guide 17 may be subjected to a surface roughening processing to be provided as heat conversion portions 27, 28, respectively, as shown in FIGS. 23 and 24.

The heat conversion portions 27, 28 subjected to the surface roughening processing is subjected to a graining processing such as of the so-called frosted glass, e.g., thus enabling more efficiently converting the illumination light from the light guide 17 to heat.

The above-mentioned part of the cover glass 15 and the surface of the protruding portion 35, which are subjected to the surface roughening processing into the heat conversion portions 27, 28, respectively, may be either on a front surface side configuring a part of the distal end surface of the distal end portion 2, or a back surface side opposed to the irradiating surface 17a of the light guide 17, as shown in FIGS. 25 and 26.

In FIG. 25, if the surface of the heat conversion portions 27, 28 that is subjected to the surface roughening processing is on the front surface, the illumination light generates heat in the vicinity of the glass surface portion 15a of the cover glass 15 on which moisture condensation occurs. Thus, the amount of heat for preventing moisture condensation can be efficiently conducted to the glass surface portion 15a of the cover glass 15.

On the other hand, as shown in FIG. 26, if the surface of the heat conversion portions 27, 28 subjected to the surface roughening processing is on the back side, illumination light before incident into the cover glass 15 causes the heat conversion portions 27, 28 to generate heat. Thus, it is enabled to reduce lens flare caused by scattered light of the illumination light incident into the optical lens group 18 through the cover glass 15.

Note that, as mentioned above, the heat conversion portions 27, 28 are not to be subjected limitatively to the surface roughening processing but are sufficed to be configured to efficiently convert the illumination light to heat and may be processed to be colored in, e.g., black, gray, purple, etc.

The heat conversion portions 27, 28, in addition to be configured to efficiently convert the illumination light to heat, may further be subjected to a multi-coating, antireflection (AR) coating, etc., with silicon dioxide ($SiO_2$), magnesium fluoride ($MgF_2$), etc., for preventing lens flare by the illumination light as mentioned above. Providing each of these coats can better the light transmittance and improve light amount of the illumination light attenuated by the heat conversion.

Furthermore, to prevent lens flare by the illumination light, the heat conversion portions 27, 28 may have a surface having a minute uneven structure with an antireflection effect as shown in FIG. 27. To describe in detail, the surface having a minute uneven structure having an antireflection effect refers to a surface arranged with a countless number of structures of, e.g., triangular pyramids each having a size not greater than a light wavelength, with a length of one side of 10 s nm to 300 nm and a height of 10 s nm to 500 nm. Note that the minute uneven structures with antireflection effect are not limited to triangular pyramids but may be circular cones, quadrangular pyramids, polyhedral cones, etc.

The minute uneven structure having an antireflection effect can restrain reduction of the transmittance of the illumination light, by means of the uneven structures each sized not greater than that of a light wavelength.

The above-described configuration for heat conversion with the illumination light of the light guide 17 is not to be limitatively applied to the rigid endoscope 1, but may also be applied to the flexible endoscope 40 as shown in FIG. 28. Specifically, there is provided a heat conduction portion 56 that integrally couples the observation window 51 and, here, the illumination window 52. The illumination window 52 is subjected to a surface processing with the above-described graining, coloring processing, various coatings, or minute uneven structure having an antireflection effect, and the heat heated by the illumination light is conducted to the observation window 51 through the heat conduction portion 56. Thus, the conducted heat prevents moisture condensation from occurring on the observation window 51.

In addition, to prevent lens flare, which is caused by scattered light of the illumination light incident into the optical lens group 18, the cover glass 15 may be provided inclined at a predetermined angle α relative to an optical axes O of the photographing light, as shown in FIGS. 29 and 30.

Furthermore, to prevent lens flare, an irradiating surface 17b of the light guide 17 may be diagonally cut to an extent not exerting an influence on illumination, as shown in FIG. 31. Still furthermore, there may be provided oblique steps as an irradiating surface 17c of the light guide 17, as shown in FIG. 32.

The invention described in each of the above-described embodiments is not limited to the each embodiment, but various modifications can be otherwise implemented without departing from the spirit of the invention in the practical phase. Moreover, each of the above embodiments includes various phases of inventions, and various inventions can be extracted by appropriately combining a plurality of disclosed constituent features.

For example, if the problem described in the section of problems to be solved by the invention can be solved and the effect described in the effect of the invention be acquired even if some constituent features are deleted from all the constituent features shown in each embodiment, then the configuration excluding those constituent features can be extracted as an invention.

What is claimed is:

1. An endoscope comprising:
    an insertion portion including a distal end portion having a distal end surface provided with an irradiating surface for irradiating illumination light, adapted to be inserted into a subject;
    an observation optical system disposed in the insertion portion;
    an observation window configuring a part of an outer surface of the distal end portion, through which an observation light to be incident into the observation optical system transmits;
    a first hydrophilic portion that is film-formed at least on a surface of the observation window;
    a second hydrophilic portion that is film-formed on a distal end surface of the distal end portion including the irradiating surface, except for the observation window;
    a third hydrophilic portion that is film-formed on a circumferential side surface of the distal end portion; and
    a heat conversion portion that is disposed on the observation window and converts the illumination light irradiated thereon into heat to prevent moisture condensation on the observation window, wherein the heat conversion portion on the observation window has a roughened surface on a part of the observation window that faces an irradiating surface of a light guide that transmits the illumination light.

2. The endoscope according to claim 1, wherein the first hydrophilic portion, the second hydrophilic portion, and the third hydrophilic portion are hydrophilic films that are continuously formed.

3. The endoscope according to claim 1, wherein the roughened surface has small uneven structures on a part of the observation window that faces an irradiating surface of a light guide that transmits the illumination light.

4. A hydrophilic cap comprising:
    a cylindrical body having an essentially circular ring shape, that is detachably attachable to a distal end portion of an endoscope;
    a transparent plate body disposed on a distal end of the cylindrical body;
    a hydrophilic portion that is film-formed on a distal end surface of the cylindrical body including a surface of the plate body, and on a circumferential side surface of the cylindrical body; and
    a heat conversion portion that is disposed on the plate body and converts the illumination light irradiated thereon from an endoscope into heat to prevent moisture condensation on the plate body, wherein the heat conversion portion on the observation window has a roughened surface on a part of the observation window that faces an irradiating surface of a light guide that transmits the illumination light.

5. The hydrophilic cap according to claim 4, wherein the hydrophilic portion is film-formed on an outer circumferential surface of the cylindrical body so that the surface of the plate body is continuous with the circumferential side surface.

6. The hydrophilic cap according to claim 4, wherein the roughened surface has small uneven structures on a part of the plate body that faces an irradiating surface of a light guide which transmits the illumination light.

7. An endoscope comprising:
    an insertion portion including a distal end portion, to be inserted into a subject;
    an observation optical system disposed in the insertion portion;
    an illumination optical system for irradiating illumination light to the subject;
    an optical member configuring a part of an outer surface of the distal end portion, through which an observation light to be incident into the observation optical system transmits;
    a cylindrical body having an essentially circular ring shape, that is detachably attachable to the distal end portion;
    a transparent plate body disposed on a distal end of the cylindrical body;
    a hydrophilic portion that is film-formed on a distal end surface of the cylindrical body including a surface of the plate body and on a circumferential side surface of the cylindrical body; and
    a heat conversion portion that is disposed on the optical member and converts the illumination light irradiated thereon from the illumination optical system into heat to, wherein the heat conversion portion on the observation window has a roughened surface on a part of the observation window that faces an irradiating surface of a light guide that transmits the illumination light.

8. The endoscope according to claim 7, wherein the hydrophilic portion is film-formed on an outer circumferential surface of the cylindrical body so that the surface of the plate body is continuous with the circumferential side surface.

9. The endoscope according to claim 7, wherein the roughened surface has small uneven structures on a part of the optical member that faces an irradiating surface of a light guide which transmits the illumination light.

* * * * *